United States Patent [19]

Haigh et al.

[11] Patent Number: 5,869,495
[45] Date of Patent: Feb. 9, 1999

[54] HETEROCYCLIC COMPOUNDS AS PHARMACEUTICAL

[75] Inventors: David Haigh, Horsham; John Thomas Sime, Dorking, both of England

[73] Assignee: SmithKline Beecham p.l.c., Brentford, England

[21] Appl. No.: 458,335

[22] Filed: Jun. 2, 1995

Related U.S. Application Data

[63] Continuation of Ser. No. 360,755, Mar. 9, 1995, abandoned.

[30] Foreign Application Priority Data

| Jul. 3, 1992 | [GB] | United Kingdom | 9214185 |
| Dec. 29, 1992 | [GB] | United Kingdom | 9227030 |
| May 28, 1993 | [GB] | United Kingdom | 9311027 |

[51] Int. Cl.⁶ .................. A61K 31/505; C07D 239/42
[52] U.S. Cl. .................. 514/275; 514/260; 544/292; 544/331; 544/332
[58] Field of Search .................. 514/260, 275; 544/292, 330, 331, 332

[56] References Cited

U.S. PATENT DOCUMENTS

| 5,002,953 | 3/1991 | Hindley | 514/275 |
| 5,089,514 | 2/1992 | Hulin | 514/374 |
| 5,194,443 | 3/1993 | Hindley | 514/367 |
| 5,232,925 | 8/1993 | Hindley | 514/272 |

FOREIGN PATENT DOCUMENTS

| 0306228 | 3/1989 | European Pat. Off. |
| WO91/19702 | 12/1991 | WIPO |
| WO92/02520 | 2/1992 | WIPO |

OTHER PUBLICATIONS

Itoh et al., J. Org. Chem., vol. 56, pp. 797–804 (1991).
March, Advanced Organic Chemistry, John Wiley & Sons, pp. 334–336 (1985).

*Primary Examiner*—Yogendra N. Gupta
*Attorney, Agent, or Firm*—Charles M. Kinzig

[57] ABSTRACT

A compound of Formula (I)

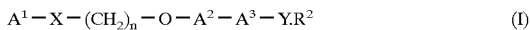

or a tautomeric form thereof and/or a pharmaceutically acceptable salt thereof, and/or a pharmaceutically acceptable solvate thereof, wherein $A^1$, $A^2$, $A^3$, $R^2$, X, Y and n are as defined herein; a pharmaceutical composition comprising such a compound and the use of such a compound or composition in medicine.

13 Claims, No Drawings

HETEROCYCLIC COMPOUNDS AS PHARMACEUTICAL

This is a continuation of application Ser. No. 08/360,755, filed Mar. 9, 1995, now abandoned.

This invention relates to certain novel compounds, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581, 0208420, 0306228 and International Patent Application Publication No. WO 9101337 relate to thiazolidinedione derivatives which are disclosed as having hypoglycaemic and hypolipidaemic activity. Chem. Pharm. Bull 1982, 30 (10) 3580–3600 relates to certain thiazolidinedione derivatives having hypoglycaemic and hypolipidaemic activities.

International Patent Application, Publication Number WO 91/19702 discloses compounds of formula (A) and (B):

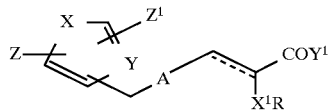  (A)

and

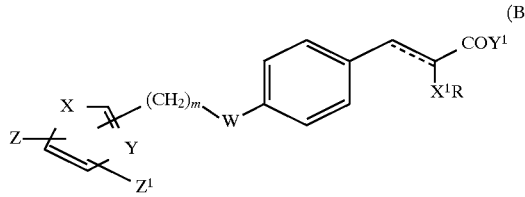  (B)

wherein A is

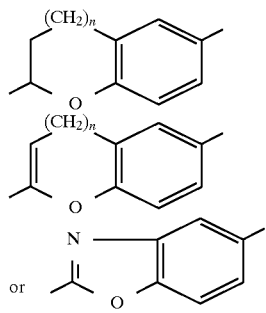

n is 0 or 1;
m is 0, 1 or 2;
— represents a bond or no bond;
R is $(C_1-C_8)$alkyl, $(C_3-C_7)$cycloalkyl, $(C_3-C_8)$alkenyl, $(C_3-C_8)$alkynyl, phenyl, $(C_7-C_8)$phenylalkyl, $(C_2-C_8)$alkanoyl, or one of said groups mono- or disubstituted with $(C_1-C_3)$alkyl, trifluoromomethyl, hydroxy, $(C_1-C_3)$alkoxy, fluoro or chloro;
W is O, CO, $CH_2$, CHOH or —CH=CH—;
X is S, O, $NR^2$, —CH=CH—, —CH=N— or —N=CH—'
$R^2$ is hydrogen, $(C_1-C_3)$alkyl, phenyl or benzyl;
Y is CH or N;
Z is H, amino, $(C_1-C_7)$alkyl, $(C_3-C_7)$cycloalkyl, phenyl, or phenyl mono- or disubstituted with $(C_1-C_3)$alkyl, trifluoromethyl, $(C_1-C_3)$alkoxy, phenyl, phenoxy, benzyl, benzyloxy, fluoro or chloro;
$Z^1$ is hydrogen or $(C_1-C_3)$alkyl;
$X^1$ is O, S, SO or $SO_2$; and $Y^1$ is hydroxy, $(C_1-C_3)$alkoxy, phenoxy, benzyloxy, amino, $(C_1-C_4)$alkanoylamino, $(C_1-C_4)$alkanesulfonylamino, benzenesulfonylamino, naphthalenesulfonylamino, di[$(C_1-C_3)$alkyl]aminosulfonylamino, or one of said groups mono- or disubstituted with $(C_1-C_3)$alkyl, trifluoromethyl, hydroxy, $(C_1-C_3)$alkoxy, fluoro or chloro; the pharmaceutically-acceptable cationic salts thereof when $Y^1$ is hydroxy; and the pharmaceutically-acceptable acid addition salts thereof when the compounds contain a basic nitrogen atom.

The compounds of formula (A) are stated to be useful as hypoglycaemic and hypochlolesterolemic agents.

It has now surprisingly been discovered that certain novel compounds, structurally distinct from the abovementioned compounds, show particularly good blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia and hypertension. They are also indicated to be of use in the treatment and/or prophylaxis of cardiovascular disease, especially atheroselerosis. In addition these compounds are considered to be useful for treating certain eating disorders, in particular the regulation of appetite and food intake in subjects suffering from disorders associated with under-eating, such as anorexia nervosa, and disorders associated with over-eating, such as obesity and anorexia bulimia.

Accordingly, the present invention provides a compound of formula (I):

$$A^1-X-(CH_2)_n-O-A^2-A^3-Y.R^2 \qquad (I)$$

or a tautomeric form thereof and/or a pharmaceutically acceptable salt thereof, and/or a pharmaceutically acceptable solvate thereof, wherein:
$A^1$ represents a substituted or unsubstituted aromatic heterocyclyl group;
$A^2$ represents a benzene ring having three optional substituents;
$A^3$ represents a moiety of formula —$(CH_2)_m$—CH$(OR^1)$— wherein $R^1$ represents substituted or unsubstituted alkyl, aryl, aralkyl or alkylcarbonyl and m represents an integer in the range of from 1 to 5, or $A^3$ represents a moiety of formula —$(CH_2)_{m-1}$—CH=C$(OR^1)$— wherein $R^1$ and m are as defined above;
$R^2$ represents $OR^3$ wherein $R^3$ represents hydrogen, alkyl, aryl or aralkyl or $R^2$ represents an aromatic heterocyclyl group or —$NR^4R^5$ wherein $R^4$ and $R^5$ each independently represent hydrogen, alkyl or alkylcarbonyl or $R^4$ and $R^5$ together with the nitrogen atom to which they are attached form a heterocyclic ring, providing that $R^2$ represents an aromatic heterocyclyl group only when Y as defined below represents a bond;
X represents NR wherein R represents a hydrogen atom, an alkyl group, an acyl group, an aralkyl group wherein the aryl moiety may be substituted or unsubstituted, or a substituted or unsubstituted aryl group;
Y represents C=O or C=S or a bond providing that Y represents a bond only when $R^2$ represents the above mentioned aromatic heterocyclyl group; and
n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen.

Favoured aromatic heterocyclyl groups include substituted or unsubstituted single ring aromatic heterocyclyl groups having 5 to 7 ring atoms, preferably 5 or 6 ring atoms.

In particular, the aromatic heterocyclyl group comprising 1, 2 or 3 heteroatoms, especially 1 or 2, selected from oxygen, sulphur or nigrogen.

Suitable values for $A^1$ when it represents a 5- membered aromatic heterocyclyl group include thiazolyl and oxazolyl, especially oxazolyl.

Suitable values for $A^1$ when it represents a 6- membered aromatic heterocyclyl group include pyridyl or pyrimidinyl, especially pyridyl.

Preferably, $A^1$ represents a moiety of formula (a), (b) or (c):

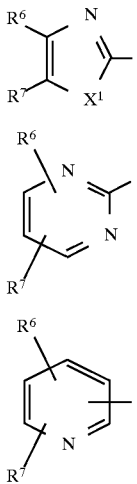

wherein:

$R^6$ and $R^7$ each independently represents a hydrogen or halogen atom, an alkyl or alkoxy group or a substituted or unsubstituted aryl group or when $R^6$ and $R^7$ are each attached to adjacent carbon atoms, then $R^6$ and $R^7$ together with the carbon atoms to which they are attached form a benzene ring wherein each carbon atom represented by $R^6$ and $R^7$ together is substituted or unsubstituted; and in the moiety of formula (a) $X^1$ represents oxygen or sulphur.

Aptly, $A^1$ represents a moiety of the abovedefined formula (a).

Aptly, $A^1$ represents a moiety of the abovedefined formula (b).

Aptly, $A^1$ represents a moiety of the abovedefined formula (c).

A particular form of moiety (c) is a moiety (c'):

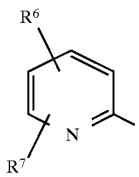

wherein $R^6$ and $R^7$ are as defined in relation to formula (c).

In one favoured aspect $R^6$ and $R^7$ together represent a moiety of formula (d):

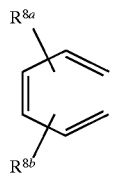

wherein $R^{8a}$ and $R^{8b}$ each independently represent hydrogen, halogen, substituted or unsubstituted alkyl or alkoxy.

Suitably, $R^8$ and $R^{8b}$ each independently represent hydrogen, halogen, alkyl or alkoxy. Favourably, $R^{8a}$ represents hydrogen. Favourably, $R^{8b}$ represents hydrogen. Preferably, $R^{8a}$ and $R^{8b}$ both represent hydrogen.

In a further favoured aspect $R^6$ and $R^7$ each independently represent hydrogen, alkyl or a substituted or unsubstituted phenyl group and more favourably, $R^6$ and $R^7$ each independently represent hydrogen, alkyl or phenyl.

Preferably for the moiety of formula (a), $R^6$ and $R^7$ together represent the moiety of formula (d).

Preferably, for the moieties of formula (b), (c) or (c), $R^6$ and $R^7$ both represent hydrogen.

Optional substituents for $A^2$ are selected from the group consisting of: halogen, substituted or unsubstituted alkyl and alkoxy.

Favourably, $A^2$ represents a moiety of formula (c):

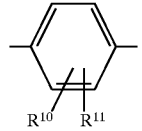

wherein $R^{10}$ and $R^{11}$ each independently represent hydrogen, halogen, substituted or unsubstituted alkyl or alkoxy.

Suitably, $R^{10}$ and $R^{11}$ each independently represent hydrogen, halogen, alkyl or alkoxy.

When $R^{10}$ or $R^{11}$ represent alkoxy, a suitable alkoxy group is a methoxy group.

Preferably, $R^{10}$ and $R^{11}$ each represent hydrogen.

Suitably, A3 represents a moiety of formula —$(CH_2)_m$—$CH(OR^1)$—.

Suitably, $A^3$ represents a moiety of formula —CH=C$(OR^1)$—.

When $R^1$ represents alkyl, suitable alkyl groups are $C_{1-6}$ alkyl groups, for example methyl, ethyl, propyl, such as a-propyl and iso-propyl, and butyl, such as t-butyl. A preferred alkyl group is an ethyl group.

When $R^1$ is substituted alkyl, particular substituents for the alkyl group include halo, hydroxy, alkoxy or a moiety —$NR^sR^t$, wherein $R^s$ and $R^t$ each independently represents hydrogen or alkyl or $R^s$ and $R^t$ together with the nitrogen atom to which they are attached form a 5- or 6- membered heterocyclic ring, or a moiety of formula —CO $X^2$ wherein $X^2$ represents OH, alkoxy or a moiety of the above defined formula —$NR^sR^t$.

Suitable haloalkyl groups include fluoroalkyl groups, such as trifluoroethyl groups.

Generally when $R^1$ is substituted alkyl, the substiuent is attached to a terminal carbon atom of the alkyl group.

when $R^1$ represents alkylcarbonyl, suitable alkylcarbonyl groups include $C_{1-6}$ alkylcarbonyl groups.

When $R^1$ represents aryl, suitable aryl groups include phenyl or naphthyl groups.

When $R^1$ represents aralkyl, suitable aralkyl groups include phenylalkyl groups for example benzyl and phenylethyl groups.

A preferred aralkyl group is a benzyl group.

Favoured substiuents for any aryl group represented by $R^1$ includes halo, alkyl and alkoxy groups; examples of such substituents include chloro, methyl and methoxy groups.

Suitably, $R^1$ represents substituted or unsubstituted alkyl or substituted or unsubstituted aralkyl.

Preferably, $R^1$ is unsubstituted alkyl or unsubstituted aralkyl.

Suitably, $R^2$ represents $OR^3$.

Suitably, $R^3$ represents hydrogen or alkyl.

When $R^3$ is alkyl, examples of $R^3$ include methyl and ethyl.

When $R^2$ is an aromatic heterocyclyl group it is suitably a single ring aromatic heterocyclyl group having 5 ring atoms, which ring atoms comprise nitrogen and optionally 1, 2 or 3 additional hetero atoms; examples include 1, 2, 4-triazole; 1, 2, 4-oxadiazole and tetrazolyl; generally the aromatic heterocyclyl group is C-linked.

Suitable substituents on the aromatic heterocyclyl group include alkyl, aryl, alkoxy and halo, an example of a substiuent is methyl.

When $-NR^4R^5$ or $-NR^sR^t$ represents a heterocyclic ring, favoured heterocyclic rings are saturated or unsaturated, fused or monocyclic heterocyclic rings comprising 5, 6 or 7 ring atoms and optionally comprising 1 or 2 additional hetero-atoms, selected from O, S or N, in each ring. Favoured rings are saturated rings. Favoured rings are monocyclic rings. Favoured, additional hetero-atoms are N or O. Examples of such heterocyclic rings include N-pyrrolidinyl, N-piperidinyl and N-morpholinyl.

A further example of $NR^4R^5$ is $NH_2$.

Suitably, $R^2$ represents $NR^4R^5$.

Preferably $R^2$ is $OR^3$.

Suitably when $R^2$ represents $OR^3$ wherein $R^3$ represents hydrogen, alkyl, aryl or aralkyl or $R^2$ represents $-NR^4R^5$, Y is CO or CS; preferably, Y is CO.

When $R^2$ is an aromatic heterocyclyl group, Y is a bond.

Suitably, R represents hydrogen or alkyl.

When R is acyl, suitable acyl groups include alkylcarbonyl groups, such as acetyl.

Suitably, m represents 1 or 2.

Favourably, m is 1.

Favourably, n is 2.

As indicated above, a compound of formula (I), and the pharmaceutically acceptable salts thereof, may exist in one of several tautomeric forms, all of which are encompassed by the present invention as individual tautomeric forms or as mixtures thereof. The compounds of formula (I) may contain at least one chiral carbon, and hence they may exist in one or more stereoisomeric forms. For example, when $A^3$ represents a moiety of formula $-(CH_2)_m-CH(OR^1)-$ the $CH(OR^1)$-carbon atom is a chiral carbon. In addition, when $A^3$ represents a moiety of formula $-(CH_2)_{m-1}-CH=C(OR^1)-$ the compounds of formula (I) exist as geometric isomers. The present invention encompasses all of the isomeric forms of the compounds of formula (I) and the pharmaceutically acceptable salts thereof, whether as individual isomers or as mixtures of isomers, including racemates.

Suitable substiuents for any heterocyclyl group include up to 4 substiuents selected from the group consisting of: alkyl, alkoxy, aryl and halogen or any two substiuents on adjacent carbon atoms, together with the carbon atoms to which they are attached, may form an aryl group, preferably a phenylene group, and wherein the carbon atoms of the aryl group represented by the sad two substituents may themselves be substituted or unsubstituted.

When used herein, unless otherwise stated, the term 'aryl' includes phenyl and naphthyl; any aryl group mentioned herein may be optionally substituted with up to five, preferably up to three, groups selected from halogen, alkyl, phenyl, alkoxy, alkylcarbonyloxy, or alkylcarbonyl groups.

When used herein the term 'halogen' refers to fluorine, chlorine, bromine and iodine; preferably chlorine.

As used herein, alkyl groups, whether present alone or as part of other groups such as alkoxy or aralkyl groups, are alkyl groups having straight or branched carbon chains, containing up to 12 carbon atoms. Thus, suitable alkyl groups are $C_{1-12}$alkyl groups, especially $C_{1-6}$alkyl groups e.g. methyl, ethyl, n-propyl, iso-propyl, n-butyl, isobutyl or tert-butyl groups.

Suitable substiuents for any alkyl group include those indicated above in relation to the term "aryl".

Favoured aralkyl groups are phenylalkyl groups, optionally substituted on the aryl or alkyl moieties as defined herein.

Suitable acyl groups include alkylcarbonyl groups.

Suitable pharmaceutically acceptable salts include salts of carboxy groups and acid addition salts.

Suitable pharmaceutically acceptable salts of carboxy groups include metal salts, such as for example aluminum, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable acid addition salts include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphonate, α-keto glutarate and α-glycerophosphate.

Suitable pharmaceutically acceptable solvates include hydrates.

The salts and/or solvates of the compounds of formula (I) may be prepared and isolated according to conventional procedures for example sodium salts may be prepared by using sodium methoxide in methanol.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (II):

$$R^a-A^2-A^{3'}-Y.R^{2'} \qquad (II)$$

wherein $A^2$ and Y are as defined in relation to formula (I): $A^{3'}$ represents a moiety of formula $-(CH_2)_m-CH(OR^{1'})-$ wherein $R^{1'}$ represents $R^1$ as defined in relation to formula (I) or a protected form thereof, and m is as defined in relation to formula (I), or $A^3$ represents a moiety of formula $-(CH_2)_{m-1}-CH=C(OR^{1'})-$ wherein $R^{1'}$ is as defined above;

$R^{2'}$ represents $R^2$ as defined in relation to formula (I) or a protected form thereof and $R^a$ is a moiety convertible to a moiety of formula (f):

   (f)

wherein $A^1$, X and n are as defined in relation to formula (I); with an appropriate reagent capable of converting $R^a$ to the said moiety (f) and thereafter, if required, carrying out one or more of the following optional steps:

(i) converting a compound of formula (I) to a further compound of formula (I);

(ii) removing any necessary protecting group;

(iii) preparing a pharmaceutically acceptable salt of the compound of formula (I) and/or a pharmaceutically acceptable solvate thereof.

Suitably, $R^a$ represents $HX$—$(CH_2)_n$—O— wherein X and n are as defined in relation to formula (I), or $R^a$ represents OH.

Preferably, $R^a$ represents OH.

When $R^a$ is $HX$—$(CH_2)_n$—O—, an appropriate reagent capable of converting $R^a$ to a moiety (f) is a compound of formula (III):

   (III)

wherein $A^1$ is as defined in relation to formula (I) and $R^x$ represents a leaving group.

A suitable leaving group $R^x$ includes a halogen atom, preferably a chlorine or bromine atom, or a thioalkyl group for example a thiomethyl group.

Generally, $R^{1'}$ is $R^1$. Preferably, $R^{2'}$ represents $OR^{3'}$ wherein $R^{3'}$ represents hydrogen, alkyl, aryl, aralkyl or $R^{2'}$ represents the above defined moiety —$NR^4R^5$.

When $R^a$ is OH, an appropriate reagent is a compound of formula (IIIA):

   (IIIA)

wherein $A^1$, X and n are as defined in relation to formula (I) and $R^y$ represents a leaving groups, such as a tosylate or mesylate group.

The reaction between the compound of formula (II) and the appropriate reagent may be carried out under conditions suitable to the particular compound of formula (II) and the reagent chosen: For example the abovementioned reaction between a compound of formula (II) wherein $R^a$ represents $HX$—$(CH_2)_n$—O— and the compound of formula (III), may be carried out in any suitable solvent, for example dimethylformamide, at a temperature which provides a suitable rate of formation of the compound of formula (I), for example at an elevated temperature in the range from 50° C. to 120° C., preferably in the presence of a base such as triethylamine.

In a further example, the reaction between the compound of formula (II) wherein $R^a$ is OH and the reagent of the abovedefined formula (IIIA) may be carried out in an aprotic solvent, such as dimethylformamide, at a low to an elevated temperature, for example in the range form 50° C. to 120° C., for example at 80° C., and preferably in the presence of a base, such as sodium hydride. In an alternative aspect, when $R^y$ in the compound of formula (IIIA) represents H and $R^a$ is OH in the compound of formula (II), then a suitable reagent is provided by diethylazodicarboxylate and triphenylphosphine; the coupling reaction may be carried out in any suitable solvent at a low to medium temperature, for example in tetrahydrofuran at a temperature in the range of between 0° and 60° C.

A compound of formula (II), wherein $A^{3'}$ represents a moiety of formula —$(CH_2)_m$—$CH(OR^{1'})$—, may be prepared by reacting a source of a carbene of formula (IV):

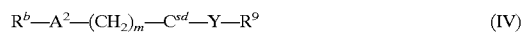   (IV)

wherein $A^2$, Y and m are as defined in relation to the compound of formula (I), $R^b$ is a moiety $R^a$ or a moiety convertible to a moiety $R^a$ and $R^9$ is the above defined $R^{2'}$ or a protecting group, with a compound of formula (V):

   (V)

wherein $R^{1'}$ is defined in relation to formula (II); and thereafter, if required, converting a moiety $R^b$ into a moiety $R^a$ and removing any protecting group.

Preferably, Y is CO. Preferably, $R^9$ is $OR^{3'}$ or —$NR^4R^5$.

A suitable source of the carbene of formula (IV) is provided by reacting a compound of formula (IVA):

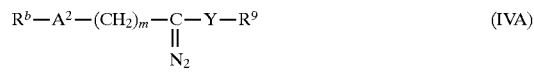   (IVA)

wherein $A^2$, $R^9$, $R^b$, Y and m are as defined in relation to formula (IV), with a rhodium (II) salt, such as rhodium (II) acetate.

The conditions used in the preparation of the carbene of formula (IV) from (IVA) will of course depend upon the particular carbene chosen, but in general conventional procedures are used, for example when (IV) is the carbene and (IVA) is the source of carbene then suitable conditions are analogous to those disclosed in Terrahedron Lett. 1973, 2233.

The reaction between the carbene of formula (IV) and the compound of formula (V) may be carried out under conventional conditions, generally in an inert solvent, such as benzene, or when practicable in compound (V) as solvent, at any temperature providing a convenient rate of formation of the required product, generally at an elevated temperature, such as the reflux temperature of the solvent: Suitably, the conditions used are analogous to those disclosed in Tetrahedron Lett., 1973, 2233.

When the source of the carbene is a compound of formula (IVA), the compound of formula (IVA) may be prepared by diazotizing a compound of formula (VI):

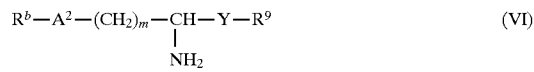   (VI)

wherein $A^2$, $R^9$, $R^b$, Y and m are as defined in relation to the compound of formula (IV), with an appropriate diazotizing agent; and thereafter, if required, converting a moiety $R^b$ into a moiety $R^a$ and removing any protecting group.

A suitable diazotizing agent is an alkyl nitrite, such as iso-amyl nitrite.

Suitable diazotising conditions for preparing the compound of formula (IVA) are conventional conditions, for example those disclosed in Tetrahedron Lett. 1971, 4495.

Any moiety $R^b$ may be converted into a moiety $R^a$ by the appropriate conventional means, for example when $R^b$ represents —OH and $R^a$ represents $HX$—$(CH_2)_n$—O— the appropriate conversion may be carried out by coupling a compound of formula (VI) wherein $R^b$ is OH with a compound of formula (g):

   (g)

wherein X and n are as defined in relation to formula (I) and $R^z$ is a protecting group and thereafter, if necessary, removing any protecting group.

The last abovementioned reaction is generally carried out in the presence of a suitable coupling agent; a suitable coupling agent being diethylazodicarboxylate and triphenylphosphine. The coupling reaction may be carried out in any suitable solvent at a low to medium temperature, for example in tetrahydrofuran at a temperature in the range of between 0° and 60° C.

Generally, for the preparation of compounds of formula (II), wherein $R^a$ is OH, from compounds of formula (IV), $R^b$ in (IV) is either OH or a protected OH, such as a benzylated OH.

The compounds of formula (V) are known commercially available compounds or they may be prepared using methods analogous to those used to prepare such compounds.

The compounds of formula (VI) are known compounds or they may be prepared using methods analogous to those used to prepare known compounds, for example those disclosed in Tetrahedron Lett., 1971, 4495, in particular the compound wherein $R^9$ is $OCH_3$, m is 1, $A^2$ is 1,4-phenylene and $R^b$ is OH is a commercially available compound.

The compounds of formula (g) are known compounds or they may be prepared using methods analogous to those used to prepare known compounds, for example those disclosed in EP0356214.

A compound of formula (I), wherein $A^3$ represents a moiety of formula —$(CH_2)_m$—$CH(OR^1)$—, or a tautomeric form thereof, and/or a pharmaceutically acceptable salt thereof and/or a pharmaceutically acceptable solvate thereof, may also be prepared by reacting an activated form of a compound of formula (VII):

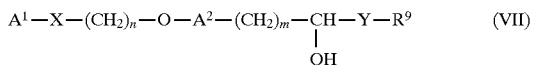

wherein $A^1$, $A^2$, X, Y, m and n are as defined in relation to formula (II) and $R^9$ is as defined in relation to formula (IV) with a compound of formula (VIII):

wherein $R^1$ is as defined in relation to formula (I) and $L^1$ represents a leaving group or atom; and thereafter if required carrying out one or more of the following optional steps:

(i) converging a compound of formula (I) into a further compound of formula (I);

(ii) removing any protecting group; and (iii) preparing a pharmaceutically acceptable salt of a compound of formula (I) and/or a pharmaceutically acceptable solvate thereof.

Suitably, $L^1$ is a halogen atom, for example a bromine atom.

A suitable activated form of a compound of formula (VII) is an anionic form such as a salted form and especially an alkali metal salted form, for example a sodium salt.

The activated form of the compound of formula (VII) may be prepared by any appropriate conventional procedure. For example, the anionic form of the compound of formula (VII) may be prepared by treating the compound of formula (VII) with a base, such as a metal hydride base, for example sodium hydride.

The reaction conditions for the reaction between the compounds of formulae (VII) and (VIII) are generally conventional alkylation conditions. For example the reaction between the salted form of a compound of formula (VII) and a compound of formula (VIII) may be carried out in an aprotic solvent, such as dimethylformamide, at any temperature providing a suitable rat of formation of the required product, generally an elevated temperature such as in the range of 40° C. to 100° C., for example 80° C.

Favourably, the formation of the activated form of (VII) from (VII)—for example the formation of a salted form of (VII)—may be carried out in-situ prior to the reaction of the activated form of (VII) with the above defined compound of formula (VIII).

A compound of formula (VII) may be prepared by reacting a compound of formula (IX):

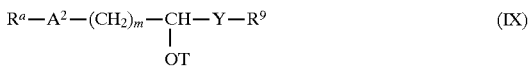

wherein $R^a$, $R^9$, $A^2$, Y and m are as defined above and T is hydrogen or a hydroxyl protecting group, with an appropriate reagent capable of converting $R^a$ to a moiety of the above defined formula (f).

The reagent capable of converting $R^a$ to a moiety of formula (f) is as defined above in relation to the formation of a compound of formula (I) from a compound of formula (II).

Suitable values for $R^a$ include those described hereinbefore.

Suitable reaction conditions for the reaction of the compound of formula (IX) and the appropriate reagent include those described above in relation to the preparation of compound (II) with the said appropriate reagent.

Preferably, in the compound of formula (IX), $R^a$ represents a hydroxyl group and a particularly appropriate reagent is the above defined compound of formula (IIIA).

The reaction between the compound of formula (IX), wherein $R^a$ is an hydroxyl group, and the reagent of the abovedefined formula (IIIA) may be carried out in an aprotic solvent, such as dimethylformamide, at a low to an elevated temperature, for example in the range of from 50° C. to 120° C., for example at 80° C., and preferably in the presence of a base, such as sodium hydride.

The compounds of formula (IX), wherein $R^a$ is OH, are known compounds or they are compounds prepared by methods analogous to those used to prepare known compounds, for example those disclosed in Dictionary of Organic Compounds 5th Edition, Vol. 3, p. 3222. Chapman & Hall, or D. H. Willimas et. at. J. Chem. Soc., Section B, 1969, 439, or J. March, Advanced Organic Chemistry, 3rd Edition (1985), Wiley Interscience or for example those disclosed in International Application, Publication No. WO92/02520.

A compound of formula (I), wherein $A^3$ represents a moiety of formula —$(CH_2)_m$—$CH(OR^1)$—, or a tautomeric form thereof, and/or a pharmaceutically acceptable salt thereof and/or a pharmaceutically acceptable solvate thereof, may also be prepared by reacting a source of a carbene of formula (X):

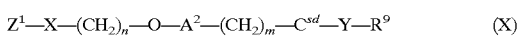

wherein $Z^1$, $A^2$, X, Y, m and n are as defined in relation to formula (I) and $R^9$ is as defined in relation to formula (IV), with a compound of the above defined formula (V); and thereafter, if required, carrying out one or more of the following optional steps:

(i) converting a compound of formula (I) into a further compound of formula (I);

(ii) removing any protecting group; and (iii) preparing a pharmaceutically acceptable salt of a compound of formula (I) and/or a pharmaceutically acceptable solvate thereof.

A suitable source of a carbene of formula (X) is provided be reacting a compound of formula (XI):

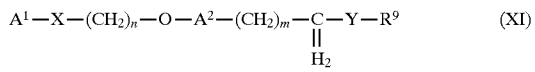

$$A^1-X-(CH_2)_n-O-A^2-(CH_2)_m-\underset{\underset{H_2}{\|}}{C}-Y-R^9 \qquad (XI)$$

wherein $A^1$, $A^2$, $R^9$, X, Y, m and n are as defined in relation to formula (X) with a rhodium (II) salt, such as a rhodium (II) acetate.

The carbene of formula (X) may be prepared from the compound of formula (XI) by using an analogous procedure to that used for the preparation of the carbene of formula (IV) from the compound of formula (IVA).

The reaction conditions for the reaction between the compounds of formulae (X) and (V) are equivalent to those used in the reaction between the compounds of formulae (IV) and (V).

The compound of formula (XI) may be prepared by reaction between the compounds of formulae (IIIA) and (VI) using an analogous procedure so that used for the preparation of the compound of formula (I) from the compounds of formulae (II) and (IIIA) and thereafter diazotized as described above for the conversion of (VI) to (IVA).

A compound of formula (I) wherein $A^3$ represents a moiety of formula —$(CH_2)_{m-1}$—CH=C(OR$^r$)— or —$(CH_2)_m$—CH(OR$^1$)—, or a tautomeric form thereof, and/or a pharmaceutically acceptable salt thereof and/or a pharmaceutically acceptable solvate thereof, may also be prepared by reacting a compound of formula (XII):

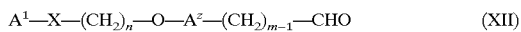

$$A^1-X-(CH_2)_n-O-A^2-(CH_2)_{m-1}-CHO \qquad (XII)$$

wherein $A^1$, $A^2$, X, m and n are as defined in relation to formula (I), with a reagent capable of converting the CHO carbon atom into a group of the above defined formula CH=C(OR$^1$)—Y.R$^2$, and thereafter, if required, reducing the group —CH=C(OR$^1$)— to provide a compound wherein $A^3$ represents a moiety of formula —$(CH_2)_m$—CHOR$^1$— and thereafter, if required, carrying out one or more of the following optional steps:

(i) converting a compound of formula (I) into a further compound of formula (I):

(ii) removing any protecting group; and (iii) preparing a pharmaceutically acceptable salt of a compound of formula (I) and/or a pharmaceutically acceptable solvate thereof.

A suitable reagent capable of converting the CHO carbon atom into a group of the above defined formula —CH=C(OR$^1$)—Y.R$^2$ is a Wittig reagent or preferably a Wadsworth Emmons reagent of formula (XIII):

$$(R^{10}O)_2P-CH\underset{YR^2}{\overset{OR^{1'}}{\diagup}} \qquad (XIII)$$

wherein $R^{1'}$, $R^{2'}$ and Y are as defined in relation to formula (II) and $R^{10}$ represents a $C_{1-6}$alkyl group, preferably a methyl or ethyl group.

The reaction between the compounds of formula (XII) and (XIII) may be carried out under conventional Wadsworth Emmons reaction conditions, for example in an aprotic solvent, such as tetrahydrofuran, at low to ambient temperature, such as in the range of from 0° to 25° C., conveniently at ambient temperature, preferably in an inert atmosphere and under anhydrous conditions. Preferably the compound of formula (XIII) is suitably activated, for example by the addition of a base such as sodium hydride or n-butyl lithium, prior to the addition of the compound of formula (XII).

The reaction of a compound wherein $A^3$ represents a moiety of formula —$(CH_2)_{m-1}$—CH=C(OR$^1$)— to provide a compound wherein $A^3$ represents a moiety of formula —$(CH_2)_m$—CH(OR$^1$)— may be carried out using conventional reduction methods, such as catalytic reduction using for example a 10% palladium-on-carbon catalyst in an alkanolic solvent such as ethanol, or by use of a metal/solvent system such as magnesium metal/methanol as described in Tet. Lett. 1986, 27, 2409.

A compound of formula (XII) may be prepared from a compound of formula (XIIA):

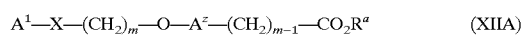

$$A^1-X-(CH_2)_m-O-A^z-(CH_2)_{m-1}-CO_2R^a \qquad (XIIA)$$

wherein $A^1$, $A^2$, X, m and n are as defined in relation to formula (I) and $R^a$ represents hydrogen or a $C_{1-6}$alkyl group, suitably a methyl group, by conventional methods for converting an ester group into a carbonyl group; one convenient method involves reducing the ester group to give a primary alcohol using for example a metal hydride reducing agent such as lithium aluminum hydride in tetrahydrofuran, and thereafter oxidising the primary alcohol to give the required carbonyl group by use of an oxidising reagent such as pyridine-sulphur trioxide complex in dimethylsulphoxide.

A compound of formula (XIIA) may be prepared from a compound of formula (XIIB):

$$HO-A^2-(CH_2)_{m-1}-CO_2R^a \qquad (XIIB)$$

wherein $A^2$, m and $R^a$ are as defined in relation to formula (XIIA), with a compound of the above defined formula (IIIA).

Suitably reaction conditions for the reaction between the compounds of formulae (IIIA) and (XIIB) are those described above for the reaction between the compounds of formulae (II) and (IIIA).

A compound of formula (II) wherein $A^{3'}$ represents a moiety of formula —CH=C(OR$^1$)— or —$CH_2$—CH(OR$^{1'}$)—, or a tautomeric form thereof, and/or a pharmaceutically acceptable salt thereof and/or a pharmaceutically acceptable solvate thereof, may be prepared by reacting a compound of formula (XIV):

$$R^b-A^2-CHO \qquad (XIV)$$

wherein $R^b$ and $A^2$ are as defined in relation to formula (IV), with a reagent capable of converting the CHO carbon atom into a group of the above defined formula —CH=C(OR$^{1'}$)—Y.R$^{2'}$; and thereafter, if required, reducing the group —CH=C(OR$^1$)— to provide a group of formula —$CH_2$—CHOR$^{1'}$; and thereafter, if required, removing any protecting group.

Preferably, $R^b$ is a protected OH group.

A suitable reagent capable of converting the CHO carbon atom of compound (XIV) into a group of the above defined formula —CH=CH(OR$^{1'}$)—Y.R$^{2'}$ is a compound of the above defined formula (XIII) in optionally protected form as defined by the nature of $R^{1'}$ and $R^{2'}$ in the required compound of formula (II).

Suitable conditions for the reaction between the compound of formula (XIV) and the said reagent are analogous to those described above for the reaction between the compounds of formulae (XII) and (XIII).

The compounds of formula (XII), in particular those wherein m is 1, may also be prepared by methods disclosed in EP0306228.

The compounds of formula (XIIB) are known commercially available compounds or they are compounds prepared by analogous methods used to prepare such compounds or they may be prepared from such compounds, for example by converting a commercially available carboxylic acid into an alkyl ester.

The compounds of formula (XIII), are known compounds or they are compounds prepared by methods analogous to those used to prepare known compounds, for example those disclosed in Annalen Chemie 1966, 699, 53 or J. Org. Chem. 1983, 48, 3408.

The compounds of formulae (XIV) are known compounds or they are compounds prepared by methods analogous to those used to prepare known compounds, for example those disclosed in EP 0306228.

A compound of formula (I), wherein $A^3$ represents a moiety of formula —$CH_2$—$CH(OR^1)$— wherein $R^1$ represents alkyl, or a tautomeric form thereof, and/or a pharmaceutically acceptable salt thereof and/or a pharmaceutically acceptable solvate thereof, may also be prepared by hydrolysing a compound of formula (XV):

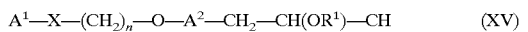

$$A^1—X—(CH_2)_n—O—A^2—CH_2—CH(OR^1)—CN \qquad (XV)$$

wherein $A^1$, $A^2$, $R^1$, X and n are as defined in relation to formula (I) to provide a compound of formula (I) wherein $R^2$ represents OH; and thereafter, if required, converting $R^2$ as Oh into another $R^2$; and thereafter, if required, carrying out one or more of the following optional steps:

(i) converting a compound of formula (I) into a further compound of formula (I);

(ii) removing any protecting group; and (iii) preparing a pharmaceutically acceptable salt of a compound of formula (I) and/or a pharmaceutically acceptable solvate thereof.

The hydrolysis of the compound of formula (XV) may be carried out using conventional conditions and reagents for nitrile hydrolysis, for example basic hydrolysis using 10% sodium hydroxide in methanol.

The conversion of $R^2$ as OH into another $R^2$ may be effected by using any convenient method, such as those methods described hereinafter.

A compound of formula (XV) may be prepared from a compound of formula (XVI):

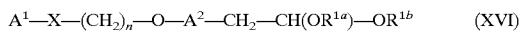

$$A^1—X—(CH_2)_n—O—A^2—CH_2—CH(OR^{1a})—OR^{1b} \qquad (XVI)$$

wherein $A^1$, $A^2$, X and n are as defined in relation to formula (I) and $R^{1a}$=$R^{1b}$ which represents alkyl; by reaction with trimethylsilylcyanide.

The reaction between the compounds of formulae (XVI) and trimethylsilylcyanide may be carried out in an inert solvent, such as dichloromethane, at low to ambient temperature, conveniently at ambient temperature and preferably in the presence of a Lewis acid catalyst, such as boron trifluoride etherate.

A compound of formula (XVI) may be prepared from a compound of formula (XVII):

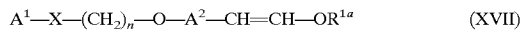

$$A^1—X—(CH_2)_n—O—A^2—CH=CH—OR^{1a} \qquad (XVII)$$

wherein $A^1$, $A^2$, $R^{1a}$, X and n are as defined in relation to formula (XV); by reaction with a compound of formula (XVIII):

$$R^{1a}—OH \qquad (XVIII)$$

wherein $R^{1a}$ is as defined above.

The reaction between the compounds of formulae (XVII) and (XVIII) is suitably carried out using the compound of formula (XVIII) as solvent, generally at an elevated temperature such as the reflux temperature of the solvent and preferably in the presence of p-toluenesulphonic acid.

Preferably, $R^{1a}$ is methyl.

A compound of formula (XVII) may be prepared by reaction of the above defined compound of formula (XII), wherein m is 1, with a reagent capable of converting the CHO carbon atom of formula (XII) into a group of the above defined formula —CH=CH—$OR^1$, the reagent being suitably a Wittig reagent of formula (XIX):

$$[Ph_3PCH_2—OR^1]^+ \; Cl^- \qquad (XIX)$$

wherein $R^1$ is as defined in relation to formula (I).

The reaction between the compounds of formulae (XII) and (XIX) may be carried out under conventional Wittig reaction conditions, for example in an aprotic solvent, such as tetrahydrofuran, at low to ambient temperature, such as in the range of from −10° to 25° C., conveniently at ambient temperature and, preferably, in an inert atmosphere under anhydrous conditions. Preferably, the compound of formula (XIX) is suitably activated by, for example, the addition of a base such as dosium hydride, n-butyl lithium or lithium diisopropylamide, prior to the addition of the compound of formula (XII).

The compounds of formula (XVIII) and (XIX) are known compounds or they are compounds prepared by methods analogous to those used to prepare known compounds, for example those disclosed in J. March. Advanced Organic Chemistry, 3rd Edition (1985). Wiley Interscience. A compound of formula (I), wherein $A^3$ is $(CH_2)_m$—$CH(OR^1)$— and $R^2$ is a C-linked aromatic heterocyclyl group, or a tautomeric form thereof, and/or a pharmaceutically acceptable salt thereof, and/or a pharmaceutically acceptable hydrate thereof, may be prepared by reacting a compound of the above defined formula (XII) with an activated form of a compound of formula (XX)

wherein het—CH is an aromatic heterocyclic group represented by $R^2$ which contains at least 1 carbon atom and thereafter converting the compound wherein $R^1$ is hydrogen into another $R^1$; and thereafter if required:

(i) converting a compound of formula (I) to a further compound of formula (I);

(ii) removing any necessary protecting group;

(iii) preparing a pharmaceutically acceptable salt of the compound of formula (I) and/or a pharmaceutically acceptable solvate thereof.

A suitable activated form of a compound of formula (XX) is a salted form such as a lithium salted form.

The activated form of a compound of formula (XX) may be prepared by reacting an aromatic heterocyclic group Het—CH or Het—CL, wherein L is a leaving group such as halogen, with an appropriate, conventional activating agent such as a salting agent, for example an alkyl lithium, in an aprotic solvent such as tetrahydrofuran according to known methods and procedures for example those disclosed in Adv. Heterocyclic chem., 1993, 56, 155.

Compounds of formula (I) wherein $A^3$ $(CH_2)_m$—CH$(OR^1)$- and $R^2$ is a C-linked tetrazolyl group or a tautomeric form thereof, and/or a pharmaceutically acceptable salt thereof, and/or a pharmaceutically acceptable hydrate thereof, wherein the heterocyclyl group may be prepared by reacting a compound of formula (XXI)

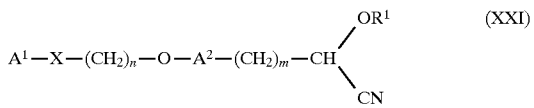
(XXI)

wherein $A^1$, $A^2$, $R^1$, X, m and n are as defined in relation to formula (I), with a source of azide ions such as an azide salt, suitably in alkali metal azide, for example sodium azide.

The compound of formula (XXI) may be prepared by dehydrating a compound of formula (I) wherein $A^3$ is $(CH_2)_m$—$CH(OR^1)$ and $YR^2$ is $CONH_2$ using for example $POCl_3$.

The reaction between the compound of formula (XXI) and the source of azide ions may be carried out under conventional conditions for example when sodium azide is the source of azide ions the reaction may be effected in an aprotic solvent such as dimethylformamide generally at an elevated temperature, for example the reflux temperature of the solvent; preferably in the presence of trimethylsilyl chloride.

The abovementioned conversion of a compound of formula (I) into a further compound of formula (I) includes:

a) converting one group R into another group R;
b) converting one group $OR^1$ into another group $OR^1$;
c) converting one group $Y.R^2$ wherein Y is CO into another group $Y.R^2$;
d) converting one group $CO.R^2$ into another group $CS.R^2$, and
e) reducing a group —CH=$C(OR^1)$- to a group —$CH_2$—$CH(OR^1)$-.

The abovementioned conversions may as appropriate be carried out on any of the intermediate compounds mentioned herein.

The conversion of a compound of formula (I) to a further compound of formula (I) may be carried out be using any appropriate conventional procedure.

Suitable conversions of one group R into another group R include converting a group R which represents hydrogen into a group R which represents an acyl group; such conversion may be carried out using an appropriate conventional acylation procedure, for example treating an appropriately protected compound of formula (I) with an acylating agent. Thus acetic anhydride may be used to prepare the compound of formula (I) wherein R is acetyl.

Suitable conversations of one group $OR^1$ into another group $OR^1$ include the converson of one substituent into another substituent when $R^1$ represents substituted alkyl, for example the reduction of a $CO_2R''$ substituent, wherein $R''$ is $C_{1-6}$ alkyl, to provide a $CH_2OH$ substituent.

The above mentioned reduction may be carried out using any conventional reduction method, for example using boronhydride reducing agents such as sodium borohydride in a solvent such as methanol.

Suitable conversions of one group $Y.R^2$ wherein Y is CO into another group $Y.R^2$, include:

(i) hydrolysing one group $Y.OR^{3a}$ wherein $R^{3a}$ is alkyl, aryl or aralkyl into a group Y.OH, wherein Y is CO;
(ii) aminating one group $Y.R^{2b}$ wherein $R^{2b}$ is alkoxy into a group $Y.NR^4R^5$, wherein Y is CO;
(iii) halogenating the above defined group Y.OH to provide the corresponding acid halide, and then aminating the halide to provide the abovementioned group $Y.NR^4R^5$ wherein Y is CO;
(iv) esterifying a group YOH to give a group Y-Oalkyl or Y-Oaralkyl, wherein Y is CO; and
(v) converting one group $Y.NH_2$ wherein Y is CO into a group Y—C—Het wherein Y is a bond and C—Het is a C-linked aromatic heterocyclyl group.

Suitable hydrolysis methods for use in conversion c(i) are conventional ester hydrolysis methods, for example using an alkali hydroxide in aqueous methanol.

Suitable amination methods for conversion c(ii) or c(iii) include conventional methods, for example treatment with aqueous ammonia in tetrahydrofuran/methanol.

Suitable halogenation methods for conversion c(iii) include conventional methods, for example treatment with oxalyl chloride.

Suitable esterification methods for conversion c(iv) are conventional methods, thus alkyl esters may be prepared by using the appropriate alkanol, for example methanol, in the presence of an acid and aralkyl esters may be prepared by treatment of a salted YOH group, such as a sodium salt, with an appropriate aralkyl halide, for example benzyl bromide.

Suitable conversion of a group $Y.NH_2$ wherein Y is CO into a group Y—C—Het wherein Y is a bond and C—Het is a C-linked aromatic heterocyclyl group includes:

a) reaction with a hydrazine, for example hydrazine hydrate, and an amide acetal, such as dimethylformamide dimethyl acetal, to provide a 1,2,4-triazole; or
b) reaction with a hydroxylamine, for example hydroxylamine hydrochloride, and an amide acetal, such as dimethylformamide dimethyl acetal, to provide a 1,2,4-oxadiazole.

Suitable conversions of one group $CO.R^2$ into another group $CS.R^2$ May be effected using conventional methods for example by using Lawesson's reagent in a solvent such as toluene, at any temperature providing an acceptable rate of formation of the required product, conveniently at the reflux temperature of the solvent.

Suitable reductions of one group —CH=$C(OR^1)$- to a group —$CH_2CH(OR^1)$- may be carried out using any convenient reduction procedure, such as the catalytic reduction or metal/solvent reduction methods as described hereinbefore.

It will be appreciated that in any of the abovementioned reaction including the abovementioned conversions (a), (b), (c), (d) and (e) any reactive group in the substrate molecule may be protected, according to conventional chemical practice.

Suitable protecting groups in any of the abovementioned reactions are those used conventionally in the art. Thus, for example, suitable hydroxyl protecting groups include benzyl or trialkylsilyl groups.

The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide.

Where appropriate the isomeric forms of the compounds of formula (I) and the pharmaceutically acceptable salts thereof may be prepared as individual isomers using conventional chemical procedures.

However for certain compounds of formula (I) there is provided a novel process for separating optical isomers of such compounds. Indeed the newly discovered process is considered to be capable of separating optical isomers of any compound providing the chiral carbon of such compound is attached to a carboxy ester group and a group $OZ^1$ wherein $Z^1$ is alkyl, aryl or aralkyl.

Accordingly, the present invention provides a process for separating optical isomers of a compound (the substrate ester) which comprises a moiety of formula (H):

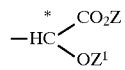

(H)

wherein C* is a chiral carbon, Z is a $C_{1-12}$ alkyl group and $Z^1$ is a $C_{1-12}$ alkyl, aryl or an aryl $C_{1-12}$ alkyl group, which process comprises enantioselectively hydrolysing the ester group $CO_2Z$ of one enantiomer into a carboxyl group with a lipase from Rhizopus delemar, Rhizopus arrhizus, Rhizopus Lip F4 or a lipase from Mucor miechei; and thereafter, as necessary, isolating either the enantiomerically enriched product carboxylic acid or the enanatiomerically enriched substrate ester.

The enantiomerically enriched product carboxylic acid and/or the enanatiomerically enriched substrate ester may be isolated using conventional extraction methods, such as phase separation and/or extraction into a suitable solvent, and thereafter, if required it may be chromatographed.

In an alternative isolation procedure, prior to isolation, the enantiomerically enriched substrate ester, may be converted by hydrolysis into the respective carboxylic acid which may then be isolated in the usual way. In one convenient aspect of the invention the enantiomerically enriched substrate ester may be hydrolysed by treatment with the abovementioned lipases to give the respective carboxylic acid.

The compounds of formula (I) which fall within formula (H) are those compounds wherein Z represents $R^3$ and $Z^1$ represents $R^1$: Thus the novel process may be used to prepare enantiomerically enriched compounds of formula (I) wherein $A^3$ represents $(CH_2)_m$—$CH(OR^1)$—, Y represents CO, $R^2$ is $OR^3$ and $A^1, A^2, R^1, R^3$ X, m and n are as defined in relation to formula (I)- (hereinafter referred to as compounds of formula (IA)).

The microbial lipase enzymes may be obtained by conventional culturing techniques such as those disclosed in J. Bacteriol., 1982, Vol. 150 498–505. H. Gilbert and M. Tully, European Patent Application No. 0198440 and British Patent No. 1,474,519. The lipase may be isolated as a pure enzyme or, in the alternative a suitable source of the lipase may be incorporated into the reaction.

Preferably, the microbial lipase enzymes are obtained commerically as purified or partially purified enzyme preparations.

The hydrolysis of the compound of formula (H) may be carried out in any suitable aqueous solvent having controlled pH, for example in an aqueous buffer or in a solvent wherein the pH is controlled by the addition of aqueous sodium hydroxide, at a pH which provides a suitable rate of formation of the required product, which is generally a pH in the range of from 5 to 9, such as in the range of from 6 to 8, for example at pH7.

The hydrolysis may be carried out at any temperature which provides a suitable rate of formation of the required product, being generally at a low to ambient temperature, such as a temperature in the range of from 5° C. to 40° C., such as in the range of from 20° C. to 40° C. and preferably in the range of from 20° C. to 30° C., for example 23° C.

Generally, the substrate mixture is introduced into the reaction system as a solution in an organic solvent which may be a water miscible solvent such as acetone, tetrahydrofuran, dimethylsulphoxide, dimethylformamide or acetonitrile.

The steroselective process selectively hydrolyses the compound (IA) having the same stereochemistry at the asterisked carbon atom as the equivalent carbon atom in (-)3-[4-2[-[N-(2-benzoxazolyl)-N-methylamino]ethoxy] phenyl]-2-methoxypropanoic acid.

The reaction conditions, such as the particular acidic pH and the reaction temperature which provide optimum enrichment for any particular enantiomerically enriched compound (H) may be determined by routine experimentation.

Suitably, the steroselective reaction provides enantiomerically enriched compound (IA) in the form wherein the required enantiomer is present in greater than 70% w/w; and favourably greater than 80% w/w. Most favourably, the product from the steroselective process provide enantiomerically enriched compound (IA) in the form wherein the required enantiomer is present as 80–100% w/w, preferably 90–100%, such as 90–95%, and most preferably 95–100%, for example 95%, 96%, 97%, 98%, 99% or 100% w/w.

The above mentioned enantiomerically enriched compound (IA) is considered to form a further aspect of the present invention. Accordingly the present invention provides enantiomerically enriched compound (IA) or a tautomeric form thereof and/or a pharmaceutically acceptable salt thereof and/or a pharmaceutically acceptable solvate thereof.

The present invention also provides enantiomerically enriched compound (IA) or a tautomeric form thereof and/or a pharmaceutically acceptable salt thereof and/or a pharmaceutically acceptable solvate thereof, wherein the required isomer is present in greater than 50% w/w; suitably greater than 70%, w/w and favourably greater than 80% w/w. Most favourably, the enantiomerically enriched compound (IA is in a form wherein 80–100% w/w, preferably 90–100%, such as 90–95%, and most preferably 95–100%, for example 95%, 97%, 98%, 99% or 100% w/w is in the form of the required isomer of a compound of formula (IA).

In one preferred aspect there is provided a compound of formula (IA) or a tautomeric form thereof and/or a pharmaceutically acceptable salt thereof and/or a pharmaceutically acceptable solvate thereof, preferably in optically pure form.

The absolute stereochemistry of compounds may be determined using conventional methods, such as X-ray crystallography.

As mentioned above the compounds of the invention are indicated as having useful therapeutic properties: The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt there and/or a pharmaceutically acceptable solvate thereof for use in the treatment of hypertension, cardiovascular disease and certain eating disorders.

Cardiovascular disease includes in particular artherosclerosis.

Certain eating disorders include in particular the regulation of appetite and food intake in subjects suffering from disorders associated with under-eating, such as anorexia nervosa, and disorders associated with over-eating, such as obesity and anorexia bulimia.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use; for example the term 'pharmaceutically acceptable salt' embraces a vertinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit does will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form there and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

No toxicological effects have been established for the compounds of formula (I) in the abovementioned dosage ranges.

The following Procedures and Examples illustrate the invention but do not limit it in any way.

EXAMPLE 1

Ethyl 3-[4-[2-[N-(2-benzoxazolyl)-N-methylamino] ethoxy]phenyl]-2-methoxypropanoate

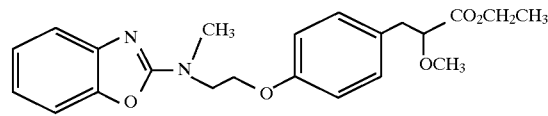

Sodium hydride (60% dispersion in oil; 0.47 g) was added portionwise to a stirred, ice-cooled solution of ethyl 3-(4-hydroxyphenyl)-2-methoxypropanoate (2.38 g) in dry N,N-dimethylformamide (50 mL) under a nitrogen atmosphere. The mixture was stirred for 30 minutes at room temperature prior to the addition of a solution of 2-[N-(2-benzoxazolyl)-N-methylamino]ethanol methanesulphonyl ester (Eur. Patent Appl. Publication No: 0306228) (2.86 g) in N,N-dimethylformamide (90 mL). The mixture was heated for 17 hrs at 80° C., cooled and concentrated in vacuo. The residue was diluted with water (200 mL) and extracted with ethyl acetate (3×200 mL). The combined organic solutions were washed with water (3×100 mL). brine (200 mL), dried (MgSO$_4$) and evaporated to afford a gum. This was chromatographed on silica gel using 10% ethyl acetate in dichloromethane as eluent to afford the title compound as a gum.

¹H NMRδ(CDCl₃) 1.22(3H, t); 2.95(2H, complex); 3.33 (3H, s); 3.34(3H, s); 3.89(1H, dd); 3.93(2H, t); 4.17(2H, q); 4.24(2H, t); 6.81 (2H, d); and 6.90–7.40 (6H, complex).

EXAMPLE 2

3-[4-[2-[N-(2-Benzoxazolyl)-N-methylamino]ethoxy]phenyl]-2-methoxypropanoic acid

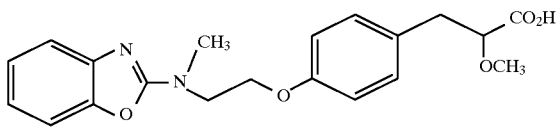

A mixture of ethyl 3-[4-[2-[N-(2-benzoxazolyl)-N-methylamino]ethoxy]-phenyl]-2methoxypropanoate (1.5 g), 10% aqueous sodium hydroxide solution (7.5 mL) and methanol (23 mL) was stirred for 1.5 hrs at room temperature and then diluted with water (600 mL), washed with dichloromethane (300 mL) and acidified to pH2 with concentrated hydrochloric acid. The mixture was extracted with ethyl acetate (3×300 mL) and the combined ethyl acetate solutions washed with water (2×200 mL) and brine (200 mL), dried (MgSO₄) and evaporated. The residue was crystallised from ethyl acetate-dichloromethane-hexane to afford the title compound, mp 150°–153° C.

¹NMRδ(CDCl₃) 2.80 (1H, dd); 2.91 (1H, dd); 3.25 (3H, s); 3.27 (3H, s); 3.83 (1H, dd); 3.90 (2H, t); 4.22 (2H, t); 675–7.40 (8H, complex); and 12.60 (1H, broad, exchanges with D₂O).

EXAMPLE 3

Methyl 3-[4-[2-[N-(2-benzoxazolyl)-N-methylamino]ethoxy]phenyl]-2-methoxypropanoate

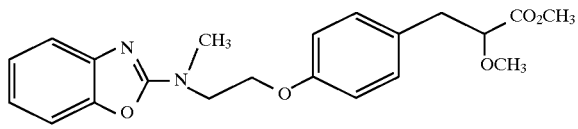

The title compound, a gum, was prepared from methyl 3-(4-hydroxyphenyl)-2-methoxypropanoate by a method similar to that described for Example 1.

¹NMRδ(CDCl₃) 2.95 (2H,complex); 3.33 (3H,s); 3.70 (3H,s); 3.90 (3H,complex); 4.24 (2H,t); 6.80 (2H,d); and 700–7.40 (6H,complex).

EXAMPLE 4

Methyl 2-methoxy-3-[4-[2-[N-methyl-N-(2-pyridyl)amino]ethoxy]-phenyl]propanoate

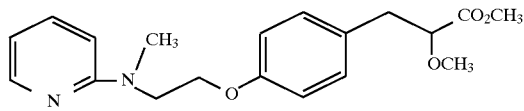

A mixture of 2-methoxy-3-[4-[2-[N-methyl-N-(2-pyridyl)amino]ethoxyl]-phenyl]propanonitrile (1.15 g), sodium hydroxide solution (10% w/v; 10 mL) and methanol (20 mL) was heated at reflux for 2.5 hrs, cooled and neutralised to pH7 with dilute HCl. The mixture was evaporated in vacuo and the residue redissolved in methanol presaturated with hydrogen chloride gas. The mixture was allowed to stand at room temperature for 7 days, then evaporated. Saturated sodium bicarbonate solution (100 mL) was added and the suspension extracted with ethyl acetate (3×200 mL). The combined ethyl acetate solutions were washed with water (2×500 mL) and brine (500 mL), dried (MgSO₄) and evaporated. The resulting gum was chromatographed on silica gel with 1% methanol in dichloromethane to afford the title compound, a gum.

¹H NMRδ(CDCl₃) 2.94 (2H,complex); 3.14 (3H,s); 3.33 (3H,s); 3.71 (3H,s); 3.94 (1H,dd); 3.96 (2H,t); 4.15 (2H,t); 6.55 (2H,complex); 6.81 (2H,d); 7.11 (2H,d); 7.45 (1H, complex); and 8.15 (1H,dd).

EXAMPLE 5

3-[4-[2-[N-(2-Benzoxazolyl)-N-methylamino]ethoxy]phenyl]-2-methoxy]propanamide

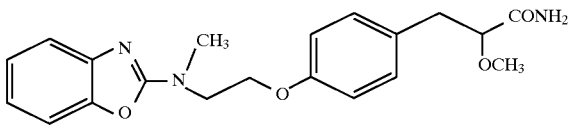

A mixture of methyl 3-[4-[2-[N-(2-benzoxazolyl)-N-methylamino]-phenyl]-2-methoxypropanoate (1.00 g), tetrahydrofuran (20 mL), methanol (20 mL) and aqueous ammonia (specific gravity 0.88; 20 mL) was stirred at room temperature for 4 hrs. A further portion of aqueous ammonia (20 mL) was added and the stirring continued at room temperature for a total of 50 hrs. The mixture was concentrated in vacuo, the residue diluted with water (500 mL) and extracted with ethyl acetate (3×200 mL). The combined ethyl acetate solutions were washed with water (500 mL), brine (500 mL), dried (MgSO₄) and evaporated. The residue was crystallised from dichloromethane-hexane to afford the title compound, mp 133°–5° C.

¹H NMRδ(CDCl₃) 2.88 (1H,dd); 3.07 (1H,dd); 3.33 (3H, s); 3.34 (3H,s); 3.80 (1H,dd); 3.94 (2H,t); 4.24 (2H,t); 5.41 (1H,br,exchanges with D₂O); 6.33 (1H,br,exchanges with D₂O); 6.80 (2H,d); 7.00 (1H,t); 7.13 (2H,d); 7.14 (1H,app. t); 7.25 (1H,d); and 7.33 (1H,d).

EXAMPLE 6

Ethyl (E/Z)-3-[4-[2-[N-(2-benzoxazolyl)-N-methylamino]ethoxy]-phenyl]-2-ethoxypropenoate

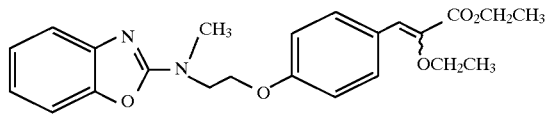

A solution of triethyl 2-ethoxyphosphonoacetate (W. Grell & H. Machleidt, *Annalen. Chemie*, 1966, 699 53) (1.98 g) in dry tetrahydrofuran (25 mL) was added slowly to a stirred, ice-cooled suspension of sodium hydride (60%) dispersion in oil; 0.33 g) in dry tetrahydrofuran (5 mL) under a nitrogen atmosphere. The mixture was stirred at 0° C. for 30 minutes prior to the addition of a solution of 4-[2-[N-(2-benzoxazolyl)-N-methylamino]ethoxy]benzaldehyde (2.19 g) in dry tetrahydrofuran (15 mL). The mixture was allowed to warm to room temperature, and stirred for a further 20 hrs. The solvent was evaporated and the residue suspended in water (300 mL) and extracted with ethyl acetate (3×250 mL). The combined ethyl acetate layers were washed with water (2×1 L), brine (1 L), dried (MgSO$_4$) and evaporated. The residue was chromatographed on silica gel with 2.5% ethyl acetate in dichloromethane as eluent to afford the title compound, a gum, as a 62:38 Z:E mixture of double bond isomers (by $^1$H NMR integration of the olefinic signals).

$^1$H NMRδ(CDCl$_3$) 1.10–1.50 (6H,complex.mixture of isomeric OCH$_2$C$\underline{H}_3$ signals); 3.35 (3Hs.N$\underline{Me}$); 3.85–4.30 (8H,complex.mixture of isomeric OC$\underline{H}_2$CH$_3$ and NC$\underline{H}_2$C$\underline{H}_2$O signals); 6.02 (0.38H*s,E-olefinic proton); 6.75–7.70 (8H,complex isomeric aromatic protons); and 6.91 (0.62H*, sZ-olefinic proton).

The two signals H* together constitute the olefinic proton signal. The assignment of the major isomer as Z (Z:E ratio is 62:38) is by analogy with reported chemical shifts of similar olefinic protons (ef R. A. Aitken and G. L. Thorn, *Synthesis*, 1989, 058).

EXAMPLE 7

Ethyl (E/Z)-3-[4-[2-benzoxazolyl)-N-methylamino] ethoxy]-phenyl]-2-phenoxypropenoate

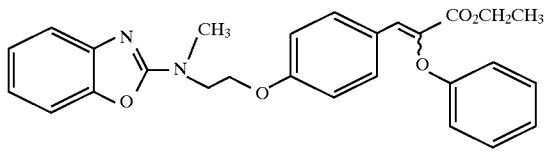

The title compound, a 1:1 mixture of double bond isomers (ratio determined by $^1$H NMR) was obtained as a gum when triethyl 2-phenoxyphosphonoacetate (0.94 g) was reacted with 4-[2-[N-(2-benzoxazolyl)-N-methylamino]ethoxy] benzaldehyde (0.89 g) in a manner similar to that described for Example 6.

$^1$H NMRδ(CDCl$_3$) 1.05 and 1.18 (combined 3H, isomeric OCH$_2$C$\underline{H}_3$ triplet signals); 3.31 and 3.35 (combined 3H, isomeric N$\underline{Me}$ singlets); 3.85–4.30 (6H, complex, isomeric OC$\underline{H}_2$CH$_3$ and NC$\underline{H}_2$C$\underline{H}_2$O signals); and 6.70–7.70 (14H, complex,aromatic and olefinic signals).

EXAMPLE 8

Ethyl 3-[4-[2-[N-(2-benzoxazolyl)-N-methylamino] ethoxy]phenyl]-2-phenoxypropanoate

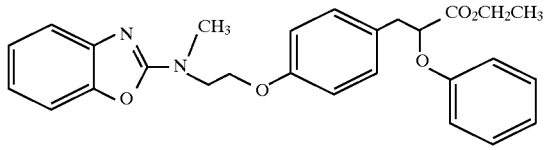

Ethyl (E/Z)-3-[4-[2-[N-(2-benzoxazolyl)-N-methylamino]ethoxy]phenyl]-2-phenoxypropenoate (0.97 g) was dissolved in dioxan (100 mL) and hydrogenated over 10% Palladium on charcoal (200 mg) at room temperature and 22 psi for a total of 7 hrs. The solution was filtered through filter aid and evaporated. The residue was chromatographed on silica gel using 5% ethyl acetate in dichloromethane as eluent to afford the title compound as a gum.

$^1$H NMRδ(CDCl$_3$) 1.18 (3H,t); 3.17 (2H,app d); 3.33 (3H,s); 3.93 (2H,t); 4.13 (2H,q); 4.25 (2H,t); 4.71 (1H,dd); 6.81 (2H,d); and 6.90–7.40 (11H,complex).

EXAMPLE 9

3-[4-[2-[N-(2-Benzoxazolyl)-N-methylamino] ethoxy]phenyl-2-phenoxypropanioc acid

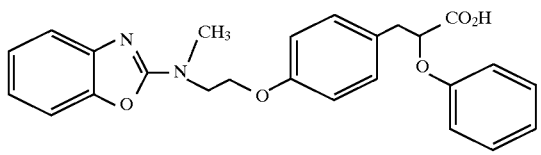

The title compound, mp 162°–4° C. (methanol) was obtained from ethyl 3-[4-[2-[N-(2-benzoxazolyl)-N-methylamino]ethoxy]phenyl]-2-phenoxypropanoate (0.88 g) by a method analogous to that described for Example 2.

$^1$H NMRδ(DMSO.d$_6$) 3.10 (2H,complex); 3.21 (3H,s); 3.87 (2H,t); 4.21 (2H,t); 4.83 (1H,dd); 6.75–7.40 (13H, complex); and 13.00 (1H,br,exchanges with D$_2$O).

EXAMPLE 10

Methyl 3-[4-[2-[N-(2-benzoxazolyl)-N-methylamino]ethoxy]phenyl]-2-ethoxypropanoate

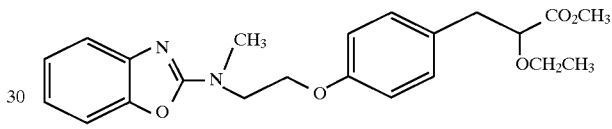

Rodium (II) acetate dimer (33 mg) was added to a mixture of methyl 3-[4-[2- [N-(2-benzoxazolyl)-N-methylamino]ethoxy]phenyl]-2-diazopropanoate (2.80 g), ethanol (2.16 mL) and benzene (50 mL). The mixture was stirred at room temperature under a nitrogen atmosphere for 15 minutes, heated at reflux for a further 15 minutes, then cooled and evaporated in vacuo. The residue was chromatographed on silica gel using 1.5% methanol in dichloromethane as eluent to afford the title compound as a gum. $^1$H NMRδ(CDCl$_3$) 1.14 (3H,t); 2.93 (2H,app d); 3.31 (1H,complex); 3.32 (3H,s); 3.57 (1H,complex); 3.69 (3H,s); 3.93 (3H,complex); 4.23 (2H,t);6.79 (2H,d); 7.00 (1H,t); 7.14 (3H,complex); 7.25 (1H,d); and 7.36 (1H,d).

EXAMPLE 11

Methyl 3-[4[-2-[N-(2-benzoxazolyl)-N-methylamino]ethoxy]phenyl]-2-isopropoxypropanoate

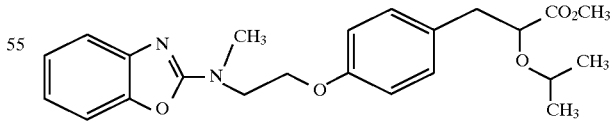

The title compound, a gum, was prepared from methyl 3-(4-hydroxyphenyl)-2-isopropoxypropanoate (1.34 g) by a method analogous to that described in Example 1.

$^1$H NMRδ(CDCl$_3$) 0.94 (3H,d); 1.13 (3H,d); 2.87 (2H, complex); 3.34 (3H,s); 3.47 (1H,complex); 3.70 (3H,s); 3.93 (2H,t); 4.00 (1H,dd); 4.23 (2H,t); 6.79 (2H,d); 7.00 (1H,t); 7.17 (3H,complex); 7.25 (1H,d); and 7.36 (1H,d).

EXAMPLE 12

Methyl 3-[4-[2-[N-(2-benzoxazolyl)-N-methylamino]ethoxy]phenyl]-2propoxypropanoate

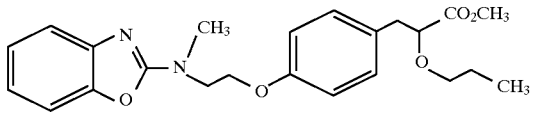

The title compound, an oil, was prepared from methyl 3-(4-hydroxyphenyl)-2-propoxypropanoate (0.88 g) by a method analogous to that described in Example 1.

$^1$H NMRδ(CDCl$_3$) 0.83 (3H,t); 1.52 (2H,complex); 2.93 (2H,complex); 3.17 (1H,complex); 3.34 (3H,s); 3.50 (1H, complex); 3.69 (3H,s); 3.85–4.00 (3H,complex); 4.22 (2H, t); and 675–7.40 (8H,complex).

EXAMPLE 13

3-[4-[2-[N-(2-Benzoxazolyl)-N-methylamino]ethoxy]phenyl-2-propoxypropanoic acid

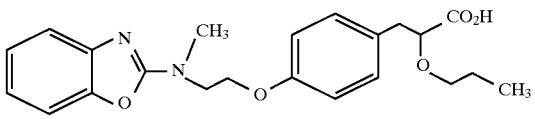

The title compound, a gum, was prepared from methyl 3-[4-[2-[N-(2-benzoxazolyl)-N-methylamino]ethoxy]phenyl]-2-propoxypropanoate (1.05 g) by a method analogous to that described in Example 2. This material was used in the salt forming step without further purification.

$^1$H NMRδ(CDCl$_3$) 0.85 (3H,t); 1.53 (2H,t); 3.00 (2H, complex); 3.29 (1H, complex); 3.32 (3H,s); 3.52 (1H, complex); 3.91 (2H,t); 4.02 (1H,dd); 4.18 (2H,t); 5.80 (1H,br,exchanges with D$_2$O); 6.77 (2H,d); and 6.95–7.40 (6H,complex).

EXAMPLE 14

3-[4-[2-[N-(2-Benzoxazolyl)-N-methylamino]ethoxy]phenyl]-2-propoxypropanoic acid, sodium salt

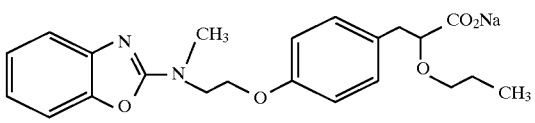

Sodium methoxide (0.11 g) was added to a stirred solution of 3-[4-[2-[N-(2-benzoxazolyl)-N-methylamino]ethoxy]phenyl]-2-propoxypropanoic acid (0.81 g) in methanol (10 mL). After stirring for 5 minutes the mixture was evaporated and then re-evaporated twice from ether (10 mL each time). The resulting gum was triturated with boiling ethyl acetate, filtered, and the filtrate concentrated and diluted with ether. The resulting solid was filtered and dried in vacuo to afford the title compound, mp 210°–4° C.

$^1$NMRδ(DMSO-d$_6$) 0.67 (3H,t); 1.35 (2H,complex); 2.65 (1H,dd); 2.85 (1H,dd); 3.02 (1H,complex); 3.25 (3H,s); 3.35 (1H,complex); 3.70 (1H,dd); 3.90 (2H,t); 4.27 (2H,t); 6.80 (2H,d); and 7.00–7.40 (6H, complex).

EXAMPLE 15

Ethyl(E/Z)-3-[4-[2-[N-(2-benzoxazolyl)-N-methylamino]ethoxy]phenyl]-2-(4-methoxyphenoxy)propenoate

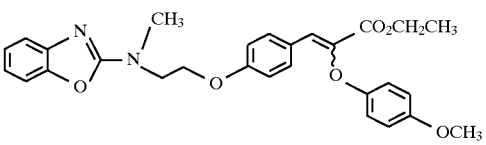

The title compound, a 1:1 mixture of double bond isomers (ratio determined by $^1$H NMR), was obtained as a gum when triethyl 2-(4-methoxyphenoxy)phosphonoacetate (2.00 g) was reacted with 4-[2-[N-(2-benzoxazolyl)-N-methylamino]ethoxy]-benzaldehyde (1.71 g) in a manner similar to that described in Example 6.

$^1$H NMRδ(CDCl$_3$) 1.08 and 1.19 (combined 3H,isomeric OCH$_2$CH$_3$ triplet signals); 3.32 and 3.34 (combined 3H,NMe singlets); 3.75 and 3.77 (combined 3H,OMe singlets); 3.95 (2H,complex); 4.05–4.35 (4H,complex); 6.55 (0.5H,s,E-isomer olefinic proton); and 6.75–7.70 (12.5H, complex).

EXAMPLE 16

Ethyl 3-[4-[2-[N-(2-benzoxazolyl)-N-methylamino]ethoxy]phenyl]-2-(4-methoxyphenoxy)propanoate

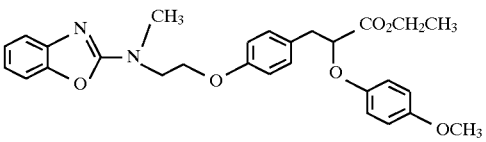

The title compound, a gum, was prepared from ethyl (E/Z)-3-[4-[2-[N-(2-benzoxazolyl)-N-methylamino]ethoxy]phenyl]-2-(4-methoxyphenoxy)propenoate by a procedure similar to that described for Example 8, using ethanol as solvent.

$^1$H NMRδ(CDCl$_3$) 1.18 (3H,t); 3.15 (2H,app. d); 3.33 (3H,s); 3.72 (3H,s); 3.93 (2H,t); 4.15 (4H,complex); 4.62 (1H,t); 6.75 (4H,s); 6.81 (2H,d); and 6.95–7.40 (6H, complex).

EXAMPLE 17

3-[4-[2-[N-(2-Benzoxazolyl)-N-methylamino]ethoxy]phenyl]-2-(4-methoxyphenoxy)propanoic acid

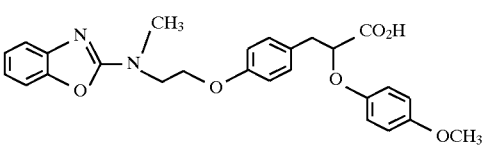

The title compound, mp 148°–50° C. (methanol), was obtained from ethyl 3-[4-[2-[N-(2-benzoxazolyl)-N-methylamino]ethoxy]phenyl]-2-(4-methoxyphenoxy)propanoate 1.62 g) by a method analogous to that described for Example 2.

$^1$H NMRδ(CDCl$_3$) 3.20 (2H,d); 3.27 (3H,s); 3.71 (3H,s); 3.85 (2H,t); 4.07 (2H,t); 4.72 (1H,t); 6.70–7.30 (12H, complex); and 9.05 (1H,br,exchanges with D$_2$O).

EXAMPLE 18

Ethyl (E/Z)-3-[4-[2-[N-(2-benzoxazolyl)-N-methylamino]ethoxy]phenyl-2-(4-methylphenoxy)propenoate

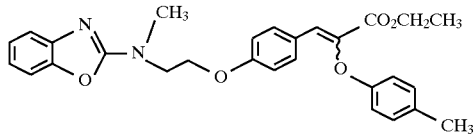

The title compound, a 1:1 mixture of double bond isomers, was prepared from triethyl 2-(4-methylphenoxy)phosphonoacetate by a method analogous to that described for Example 6, and was obtained as a gum.

$^1$H NMRδ(CDCl$_3$) 1.07 and 1.19 (combined 3H,isomeric OCH$_2$CH$_3$ triplet signals); 2.27 and 2.29 (combined 3H,Me singlets); 3.31 and 3.34 (combined 3H,NMe signals); 3.90 (2H,complex); 4.05–4.35 (4H,complex); 6.64 (0.5H,s,E-olefin isomer); and 6.75–7.70 (12.5H,complex).

EXAMPLE 19

Ethyl (E/Z)-3-[4-[2-[N-(2-benzoxazolyl)-N-methylamino]ethoxy]phenyl]-2-(4-methylphenoxy)propanoate

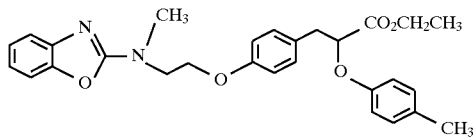

The title compound, a gum, was prepared from ethyl (E/Z)-3-[4-[2-[N-(2-benzoxazolyl)-N-methylamino]ethoxy]phenyl]-2-(4-methylphenoxy)propenoate by a procedure similar to that described for Example 8, using ethanol as solvent.

$^1$H NMRδ(CDCl$_3$) 1.18 (3H,s); 2.24 (3H,s); 3.15 (2H,complex); 3.33 (3H,s); 3.93 (2H,t); 4.17 (2H,q); 4.23 (2H,t); 4.67 (1H,t); 6.71 (2H,d); 6.81 (2H,d); and 6.95–7.40 (8H, complex).

EXAMPLE 20

3-[4-[2- [N-(2-Benzoxazolyl)-N-methylamino]ethoxy]phenyl]-2-(4-methylphenoxy)propanoic acid

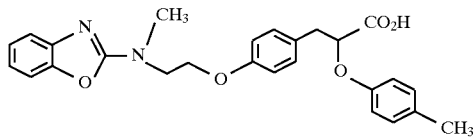

The title compound, mp 150°–151° C. (methanol), was obtained from ethyl 3-[4-[2-[N-(2-benzoxazolyl)-N-methylamino]ethoxy]phenyl]-2-(4-methylphenoxy)propanoate by a method analogous to that described for Example 2.

$^1$H NMRδ(CDCl$_3$) 2.33 (3H,s); 3.21 (2H,d); 3.26 (3H,s); 3.84 (2H,t); 4.06 (2H,t); 4.77 (1H,t); 6.75 (4H,complex); 6.95–7.30 (8H,complex); and 7.35 (1H,br,exchanges with D$_2$O).

EXAMPLE 21

Ethyl (E/Z)-3-[4-[2-[N-(2-benzoxazolyl)-N-methylamino]ethoxy]phenyl]-2-(2-methylphenoxy)propenoate

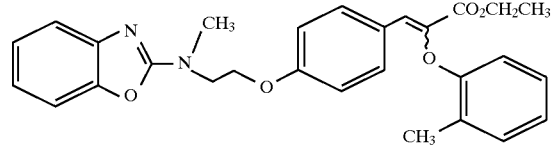

The title compound, a gum, was obtained as a 44:56 ratio of double bond isomers (as measured by $^1$H NMR) from triethyl 2-(2-methylphenoxy)phosphonoacetate by a method analogous to that described for Example 6.

$^1$H NMRδ(CDCl$_3$) 1.06 and 1.14 (combined 3H,isomeric OCH$_2$CH$_3$ triplet signals); 2.32 and 2.42 (combined 3H,methyl singlets); 3.31 and 3.34 (combined 3H,NMe singlets); 3.95 (2H,complex); 4.14 (2H,complex); 4.26 (2H, complex); 6.48 (0.44H,E-olefinic proton); 7.28 (0.56H,Z-olefinic proton); and 6.70–7.65 (12H,complex).

EXAMPLE 22

Ethyl 3-[4-[2-[N-(2-benzoxazolyl)-N-methylamino]ethoxy]phenyl]-2-(2-methylphenoxy)propanoate

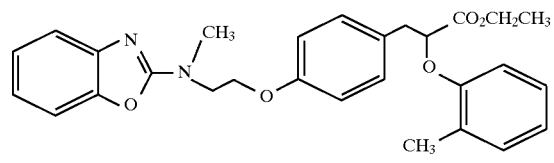

The title compound, a gum, was prepared from ethyl (E/Z)-3-[4-[2- [N-(2-benzoxazolyl)-N-methylamino]ethoxy]phenyl]-2-(2-methylphenoxy)propenoate by a procedure similar to that described for Example 8, using ethanol as solvent.

$^1$H NMRδ(CDCl$_3$) 1.18 (3H,t); 2.21 (3H,s); 3.18 (2H,d); 3.33 (3H,s); 2H,t); 4.16 (2H,q); 4.23 (2H,t); 4.72 (1H,t); 6.57 (1H,d); and 6.70–7.40 (11H,complex).

EXAMPLE 23

3-[4-[2-[N-(2-Benzoxazolyl)-N-methylamino]ethoxy]phenyl]-2-(2-methylphenoxy)propanoic acid

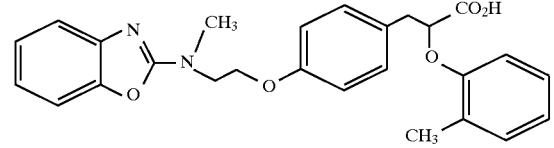

The title compound, mp 142°–3° C. (dichloromethane-hexane), was prepared from ethyl 3-[4-[2-[N-(2-benzoxazolyl)-N-methylamino]ethoxy]phenyl]-2-(2-methylphenoxy)propanoate by a method analogous to that described for Example 2.

$^1$H NMR δ(CDCl$_3$)
2.25 (3H, s); 3.25 (2H, d); 3.27 (3H, s); 3.83 (2H, t); 4.04 (2H, t); 4.82 (1H, t); 6.65–7.40 (12H, complex); and 7.88 (1H, br, exchanges with D$_2$O).

EXAMPLE 24

Methyl (E/Z)-3-[4-[2-[N-(2-benzoxazolyl)-N-methylamino]ethoxy]phenyl]-2-(4-chlorophenoxy)propanoate

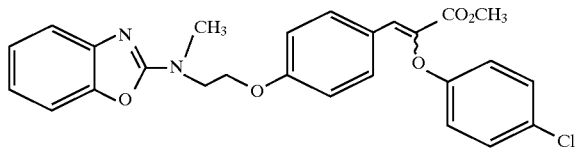

The title compound, a gum, was obtained as a 1:1 mixture of double bond isomers when methyldiethyl 2-(4-chlorophenoxy)phosphonoacetate was reacted with 4-[2-[N-(2-benzoxazolyl)-N-methylamino]ethoxy]benzaldehyde in a manner analogous to that described in Example 6.

$^1$H NMR δ(CDCl$_3$)

3.31 and 3.35 (combined 3H, NMe singles); 3.65 and 3.74 (combined 3H, OMe singlets); 3.93 (2H, complex); 4.25 (2H, complex); and 6.70–7.70 (13H, complex).

EXAMPLE 25

Methyl 3-[4-[2-[N-(2-benzoxazolyl)-N-methylamino]ethoxy]phenyl]-2-(4-chlorophenoxy)propanoate

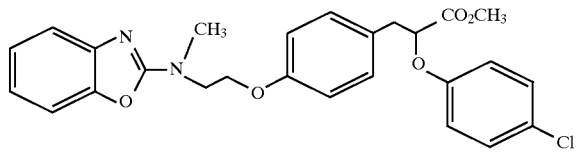

Magnesium turnings (0.5 g) were added to a mixture of methyl (E/Z)-3-[4-[2-[N-(2-benzoxazolyl)-N-methylamino]-ethoxy]phenyl]-2-(4-chlorophenoxy)propanoate (0.98 g) and a crystal of iodine dissolved in methanol (50 mL) at room temperature. The mixture was warmed gently with a heat gun until reaction ensued, at which point the heating was stopped and the mixture stirred at room temperature during the addition, over ca 5 minutes, of a further portion of magnesium (2.00 g). The reaction mixture was immersed in a cold water bath and stirring continued until all the metal had dissolved (~4 hrs), then the mixture was evaporated in vacuo. The residue was suspended in water (100 mL) and stirred vigorously during the addition of concentrated hydrochloric acid, to give (once all the suspension had dissolved) a final pH of 1.5. The mixture was extracted with ethyl acetate (2×100 mL) and the combined ethyl acetate layers then washed with water (500 mL), brine (300 mL), dried (MgSO$_4$) and evaporated. The resulting gum was chromatographed on silica gel with 3% ethyl acetate in dichloromethane as eluent to afford the title compound, mp 88°–90° C.

$^1$H NMR δ(CDCl$_3$)

3.15 (2H, d); 3.33 (3H, s); 3.69 (3H, s); 3.93 (2H, t); 4.23 (2H, t); 4.69 (1H, t); 6.73 (2H, d); 6.81 (2H, d); and 6.95–7.40 (8H, complex).

EXAMPLE 26

3-[4-[2-[N-(2-Benzoxazolyl)-N-methylamino]ethoxy]phenyl]-2-(4-chlorophenoxy)propanoic acid

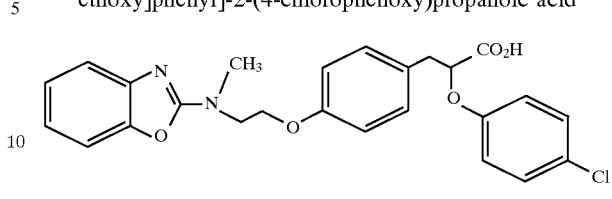

The title compound, mp 164°–5° C. (methanol), was prepared from methyl 3-[4-[2-[N-(2-benzoxazolyl)-N-methylamino]ethoxy]phenyl]-3-(4-chlorophenoxy)propanoate by a procedure analogous to that described for Example 2.

$^1$H NMR δ(CDCl$_3$)

3.22 (2H, complex); 32.6 (3H, s); 3.84 (2H, unresolved t); 4.02 (2H, unresolved t); 4.79 (1H, t); 6.75 (2H, d); 6.83 (2H, d); and 6.95–7.30 (9H, complex; reduces to 8H on shaking with D$_2$O).

EXAMPLE 27

Methyl 3-[4-[2-[N-(2-benzoxazolyl)-N-methylamino]ethoxy]phenyl]-2-(phenylmethoxy)propanoate

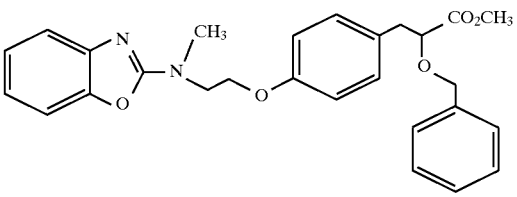

Sodium hydride (60% dispersion in mineral oil; 0.14 g) was added portionwise to a stirred solution of methyl 3-[4-[2-[N-(2-benzoxazolyl)-N-methylamino]ethoxy]phenyl]-2-hydroxypropanoate (1.20 g) in dry N,N-dimethyl formamide (20 mL) under a nitrogen atmosphere. The mixture was stirred at room temperature for 15 minutes prior to the addition of benzyl bromide (0.6 mL). Stirring was continued at room temperature for 3 hrs, then at 80° C. for 17 hrs before the mixture was cooled, diluted with water (500 mL) and extract with ethyl acetate (3×200 mL). The combined ethyl acetate layers were washed with water (4×500 mL) and brine (500 mL), dried (MgSO$_4$) and evaporated. The residue was chromatographed on silica gel with 1% methanol in dichloromethane to afford the title compound, a gum, which was used in the next stage without further purification.

$^1$H NMR δ(CDCl$_3$)

2.98 (2H, complex); 3.36 (3H, s); 3.70 (3H, s); 3.95 (2H, t); 4.07 (1H, dd); 4.25 (2H, t); 4.35 (1H, d); 4.64 (1H, d); 6.80 (2H, d); and 6.95–7.45 (11, complex).

EXAMPLE 28

3-[4-[2-[N-(2-Benzoxazolyl)-N-methylamino]
ethoxy]phenyl]-2-(phenylmethoxy)propanoic acid

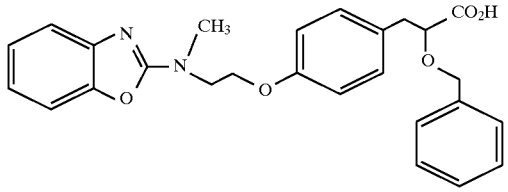

The title compound, a foam, was prepared from methyl 3-[4-[2-[N-(2-benzoxazolyl)-N-methylamino]ethoxy]phenyl]-2-(phenylmethoxy)propanoate by a procedure analogous to that described for Example 2. This material was used directly in the salt forming step without further purification.

$^1$H NMR δ(CDCl$_3$)

3.00 (1H, dd); 3.10 (1H, dd); 3.32 (3H, s); 3.90 (2H, t); 4.16 (3H, complex); 4.45 (1H, d); 4.67 (1H, d); 4.75 (1H, broad, exchanges with D$_2$O); 6.78 (2H, d); and 6.95–7.45 (11H, complex).

EXAMPLE 29

3-[4-[2-[N-(2-Benzoxazolyl)-N-methylamino]
ethoxy]phenyl]-2-(phenylmethoxy)propanoic acid,
sodium salt

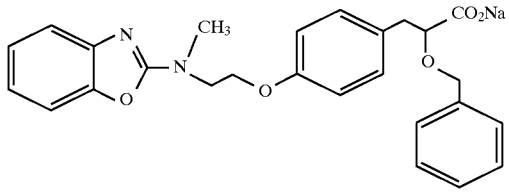

Sodium methoxide (0.031 g) was added to an ice-cooled, stirred solution of 3-[4-[2-[N-(2-benzoxazolyl)-N-methylamino]ethoxy]phenyl]-2-(phenylmethoxy)propanoic acid (0.26 g) in methanol (5 mL). The mixture was stirred at 0° C. for 10 minutes then diluted with ether (10 mL) and evaporated. The residue was stirred and re-evaporated several times from ether (10 mL each time) until a solid was obtained. The solid was filtered from ether and dried under vacuum at 60° C. for 1 week to afford the title compound, a free-flowing powder.

$^1$NMR δ(DMSO-d$_6$)

2.67 (1H, dd); 2.90 (1H, dd); 3.23 (3H, s); 3.62 (1H, dd); 3.88 (2H, t); 4.15 (1H, dd); 4.18 (2H, t); 4.63 (1H, d); 6.81 (2H, d); and 6.95–7.45 (11H, complex).

EXAMPLE 30

Ethyl (E/Z)-4-[4-[2-[N-(2-benzoxazolyl)-N-
methylamino]ethoxy]phenyl]-2-ethoxybut-2-enoate

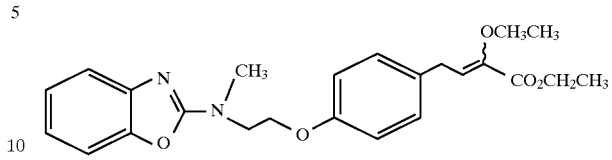

The title compound, a gum, was prepared from 4-[2-[N-(2-benzoxazolyl)-N-methylamino]ethoxy]phenylethanal by a method analogous to that described for Example 6, and was isolated as a 1:1 mixture of double bond isomers.

$^1$NMR δ(CDCl$_3$)

1.25–1.50 (6H, complex); 3.34 (3H, s); 3.50 (0.5×2H, d); 3.72 (2H, t); 3.90 (3H, complex); 4.20–4.35 (4H, complex); 5.29 (0.5H, t); 6.36 (0.5H, t); 6.78 (2H, d); and 6.90–7.40 (6H, complex).

EXAMPLE 31

Ethyl 4-[4-[2-[N-(2-benzoxazolyl)-N-methylamino]
ethoxy]phenyl]-2-ethoxybutanoate

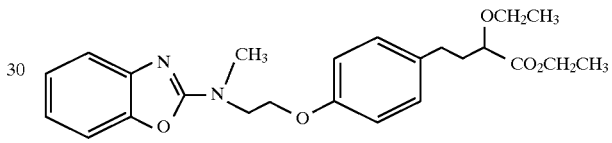

The title compound, a gum, was prepared from ethyl (E/Z)-4-[4-[2-[N-(2-benzoxazolyl)-N-methylamino]ethoxy]phenyl]-2-ethoxybut-2-enoate by a method similar to that described for Example 8, using ethanol as solvent.

$^1$H NMR δ(CDCl$_3$)

1.26 (6H, complex); 1.97 (2H, q); 2.68 (2H, complex); 3.35 (3H, s); 3.37 (1H, complex); 3.63 (1H, complex); 3.75 (1H, t); 3.94 (2H, t); 4.15–4.25 (4H, complex); 6.81 (2H, d); and 6.95–7.40 (6H, complex).

EXAMPLE 32

Ethyl (E/Z)-3-[4-[2-[N-(2-benzoxazolyl)-N-
methylamino]ethoxy]phenyl]-2-(2-napthyloxy)
propenoate

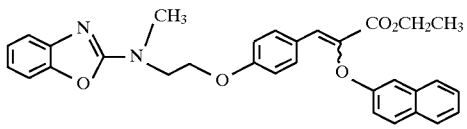

The title compound, a gum, was isolated as a 1:1 mixture of double bond isomers when triethyl 2-napthyloxyphosphonoacetate was reacted with 4-[2[N-(2-benzoxazolyl)-N-methylamino]ethoxy]benzaldehyde in a manner analogous to that described for Example 6.

$^1$NMR δ(CDCl$_3$)

1.02 and 1.15 (combined 3H; OCH$_2$CH$_3$ triplet signals); 3.27 and 3.33 (combined 3H; NMe singlets); 3.90 (2H, complex); 4.05–4.30 (4H, complex); and 6.75–7.80 (16H, complex).

EXAMPLE 33

Methyl 3-[4-[2-[N-(2-benzoxazolyl)-N-methylamino]ethoxy]phenyl]-2-(2-napthyloxy)propanoate

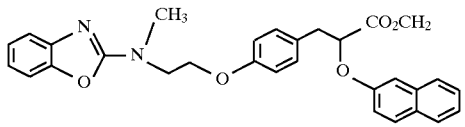

The title compound, a sticky form, was obtained from ethyl (E/Z)-3-[4-[2-[N-(2-benzoxazolyl)-N-methylamino]ethoxy]phenyl]-2-(2-napthyloxy)propenoate by a procedure analogous to that described for Example 25.

H NMR δ(CDCl$_3$)

3.23 (2H, app d); 3.31 (3H, s); 3.70 (3H, s); 3.90 (2H, t); 4.21 (2H, t); 4.91 (1H, dd); 6.81 (2H, d); and 6.90–7.80 (13H, complex).

EXAMPLE 34

3-[4-[2-[N-(2-Benzoxazolyl)-N-methylamino]ethoxy]phenyl]-2-(2-napthyloxy)propanoic acid

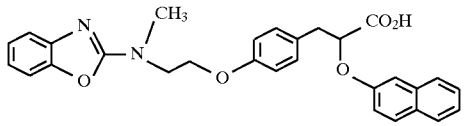

The title compound, mp 162°–4° C. (methanol), was prepared from methyl 3-[4-[2-[N-(2-benzoxazolyl)-N-methylamino]ethoxy]phenyl]-2-(2-napthyloxy)propanoate in a manner analogous to that described for Example 2.

$^1$NMR δ(DMSO-d$_6$)

3.17 (2H, complex); 3.19 (3H, s); 3.87 (2H, t); 4.21 (2H, t); 5.03 (1H, dd); 6.85 (2H, d); 6.90–7.50 (10H, complex); 7.72 (1H, d); 7.79 (2H, d); and 13.10 (1H, br, exchanges with D$_2$O).

EXAMPLE 35

Ethyl (E/Z)-2-ethoxy-3-[4-[2-[N-methyl-N-(2-pyridyl)amino]ethoxy]phenyl]-propenoate

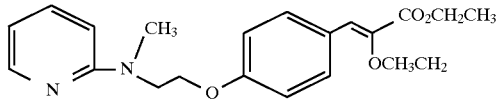

Triethyl 2-ethoxyphosphonoacetate (3.44 g) was dissolved in dry tetrahydrofuran (25 mL) and the solution added slowly to an ice-cooled, stirred suspension of sodium hydride (60% dispersion in mineral oil; 0.56 g) in tetrahydrofuran under an argon atmosphere. The mixture was stirred at 0° C. for 30 minutes prior to the addition of a solution of 4-[2-[N-methyl-N-(2-pyridyl)amino]ethoxy]benzaldehyde (Eur. Patent Appl. Publication Number EP 0306228) (3.29 g) in tetrahydrofuran (30 mL). The mixture was allowed to warm at room temperature, with stirring, over 22 hours, then concentrated in vacuo. The residue was suspended in water (300 mL), extracted with ethyl acetate (2×300 mL) and the combined ethyl acetate solutions washed with water (500 mL) and brine (500 mL), dried (MgSO$_4$) and evaporated. The residual gum was chromatographed on silica gel using 20% ethyl acetate in hexane as eluent to afford the title compound as an oil Continued elution of the chromatography column afforded a mixture comprising more of the (Z)-isomer along with the isomeric (E)-alkene (see Example 36).

$^1$N NMR δ(CDCl$_3$)

1.35 (6H, t); 3.14 (3H, s); 3.95 (4H, complex); 4.21 (2H, t); 4.28 (2H, q); 6.50 (2H, complex); 6.88 (2H, d); 6.95 (1H, s); 7.44 (1H, complex); 7.72 (2H, d); and 8.15 (1H, complex).

EXAMPLE 36

Ethyl (E)-2-ethoxy-3-[4-[2-[N-methyl-N-(2-pyridyl)amino]ethoxy]phenyl]-propenoate

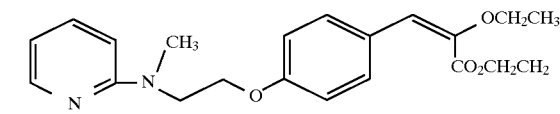

The mixture of double bond isomers obtained from the chromatography column in Example 35 was re-chromatographed, this time using 10% ethyl acetate in hexane as eluent. More of the (Z)-isomer eluted first, followed by the desired (E)-isomer, an oil.

$^1$H NMR δ(CDCl$_3$)

1.13 (3H, t); 1.40 (3H, t); 3.14 (3H, s); 3.90 (2H, q); 3.97 (2H, t); 4.15 (4H, complex); 6.06 (1H, s); 6.55 (2H, complex); 6.81 (2H, d); 7.10 (2H, d); 7.45 (1H, complex); and 8.15 (1H, complex).

EXAMPLE 37

Methyl 3-[4-[2-[N-(2-benzoxazolyl)-N-methylamino]ethoxy]phenyl]-2-(2,2,2-trifluoroethoxy)propanoate

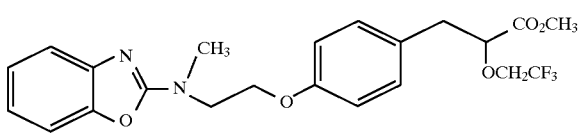

The title compound, a gum, was prepared from methyl 3-(4-hydroxyphenyl)-2-(2,2,2-trifluoroethoxy)propanoate by a method similar to that described for Example 1.

$^1$H NMR δ(CDCl$_3$)

3.00 (2H, complex); 3.34 (3H, s); 3.65 (1H, complex); 3.72 (3H, s); 3.94 (2H, t); 4.00 (1H, complex); 4.15 (1H, dd); 4.24 (2H, t); 6.81 (2H, d); and 6.95–7.40 (6H, complex).

Mass spectrum (FAB, glycerol) shows MH$^+$ at 453.1647. [C$_{22}$H$_{23}$F$_3$N$_2$O$_5$]H$^+$ requires 453.1637.

EXAMPLE 38

Methyl 2-ethoxy-3-[4-[2-[N-methyl-N-(2-pyridyl)amino]ethoxy]phenyl]-propanoate

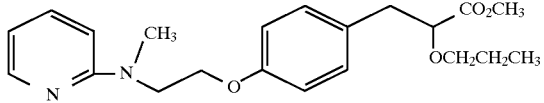

The title compound, a gum, was prepared from ethyl (Z)-2-ethoxy-3-[4-[2-[N-methyl-N-(2-pyridyl)amino]ethoxy]phenyl]propanoate by a method similar to that described for Example 25.

$^1$H NMR δ(CDCl$_3$)

1.15 (3H, t); 2.93 (2H, d); 3.14 (3H, s); 3.33 (1H, complex); 3.56 (1H, complex); 3.69 (3H, s); 3.95 (3H, complex); 4.15 (2H, t); 6.52 (2H, complex); 6.81 (2H, d); 7.11 (2H, d); 7.42 (1H, dt); and 8.13 (1H, dd).

EXAMPLE 39

Ethyl 3-[4-[2-[N-(2-benzoxazolyl)-N-methylamino]ethoxy]phenyl]-2-ethoxypropanoate

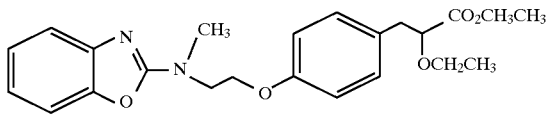

The title compound, an oil, was prepared from ethyl (E/Z)-3-[4-[2-[N-(2-benzoxazolyl)-N-methylamino]ethoxy]phenyl]-2-ethoxypropanoate by a procedure similar to that described for Example 8, using ethanol as solvent.

$^1$H NMR δ(CDCl$_3$)

1.15 (3H, t); 1.22 (3H, t); 2.92 (2H, d); 3.33 (1H, complex); 3.34 (3H, s); 3.55 (1H, complex); 3.94 (3H, complex); 4.15 (2H, q); 4.24 (2H, t); 6.80 (2H, d); and 6.95–7.40 (6H, complex).

EXAMPLE 40

3-[4-[2-[N-(2-Benzoxazolyl)-N-methylamino]ethoxy]phenyl]-2-ethoxypropanoic acid

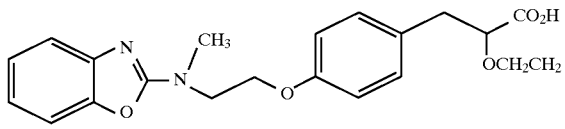

The title compound, mp 109°–110° C. (dichloromethane-hexane), was prepared from ethyl 3-[4-[2-[N-(2-benzoxazolyl)-N-methylamino]ethoxy]phenyl]-2-ethoxypropanoate by a procedure similar to that describe for Example 2.

$^1$H NMR δ(CDCl$_3$)

1.18 (3H, t); 2.98 (1H, dd); 3.04 (1H, dd); 3.32 (3H, s); 3.45 (1H, complex); 3.61 (1H, complex); 3.91 (2H, t); 4.04 (1H, dd); 4.18 (2H, t); 5.00 (1H, br, exchanges with D$_2$O); 6.80 (2H, d); and 6.95–7.40 (6H, complex).

EXAMPLE 41

3-[4-[2-[N-(2-Benzoxazolyl)-N-methylamino]ethoxy]phenyl]-2-ethoxypropanamide

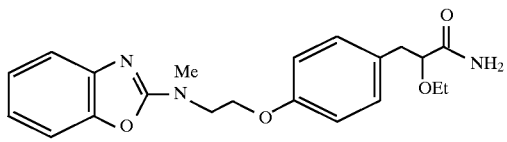

A solution of oxalyl chloride and 3-[4-[2-[N-(2-benzoxazolyl)-N-methylamino]ethoxy]phenyl]-2-ethoxypropanoic acid in dichloromethane (5 ml) was refluxed for 1½ h then concentrated. The residue was dissolved in dichloromethane and stirred with aqueous ammonia for 30 min. After extraction with chloroform (×4) the extracts were dried and concentrated. Chromatography (diethyl ether/dichloromethane) gave a white foam which was crystallised from diethyl ether m.p.=94°–95° C.

$^1$H NMR δ(CDCl$_3$)

1.12 (3H, t, J=7); 2.85 (1H, dd, J=14, 7.5) 3.07 (1H, dd, J=14, 3.5); 3.35 (3H, s); 3.37–3.55 (2H, m); 3.87 (1H, dd, J=7.5, 3.5); 3.94 (2H, t, J=5) 5.54 (1H, br s); 6.43 (1H, br s); 6.79 (2H, d, J=8.5); 7.00 (1H, dt, J=8.1); 7.15 (2H, d, J=8.5); 7.1–7.2 (1H, m); 7.24 (1H, dd, J=8.1) 7.36 (1H, d, J=8.1).

EXAMPLE 42

3-[4-[2-[N-(2-Benzoxazolyl)-N-methylamino]ethoxy]phenyl]-2-ethoxythiopropanamide

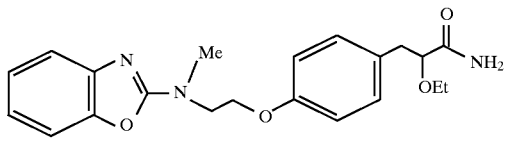

3-[4-[2-[N-(2-Benzoxazolyl)-N-methylamino]ethoxy]phenyl]-2-ethoxypropanamide (428 mg, 1.1 mmol) was suspended in toluene and Lawesson's reagent (1.1 eq) added. After 3 h at refluxed the suspension was cooled and poured into water. After extraction with chloroform (×3) the extracts were washed with aqueous ammonia, dried and concentrated. Chromatography (methanol/dichloromethane) gave the product as a white solid m.p.=46°48° C.

$^1$H NMR δ(CDCl$_3$)

1.14 (3H, t, J=7); 2.91 (1H, dd, J=14.7); 3.25 (1H, dd, J=14.3); 3.35 (3H, s); 3.35–3.51 (2H, m); 3.94 (2H, t, J=5); 4.24 (2H, t, J=5); 4.30 (1H, dd, J=7, 3.5); 6.79 (2H, d, J=8.5); 7.01 (1H, app t, J=7.5); 7.16 (2H, d, J=8.5); 7.13–7.2 (1H, obs, m); 7.25 (1H, d, J=7.5); 7.35 (1H, d, J=7.5); 7.44 (1H, br s); 7.72 (1H, br s).

EXAMPLE 43

5-[2-[4-[2-[N-(2-Benzoxazolyl)-N-methylamino]ethoxy]phenyl]-1-ethoxy]ethyl-1,2,4-triazole

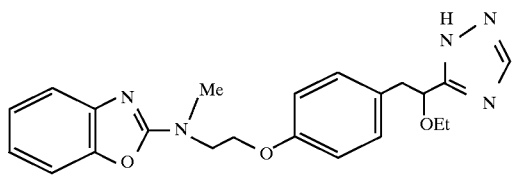

3-[4-[2-[N-(2-Benzoxazolyl)-N-methylamino]ethoxy]phenyl]-2-ethoxypropanamide (0.562 g, 1.5 mmol) in dimethylformamide dimethyl acetal was heated to 120° C. for 1½ h then cooled and concentrated. The residue was dissolved in acetic acid (4 ml) and hydrazine hydrate (1.1 eq) added. After 1½ h at 100° C. the solution was cooled, diluted with ethyl acetate and washed with water (×2) and sodium bicarbonate solution. After the solution was dried and concentrated the residue was chromatographed (methanol/dichloromethane) to give the product as a white solid m.p.=127°–129° C.

$^1$NMR δ(CDCl$_3$)

1.13 (2H, t, J=7); 3.09 (2H, dq, J=16.6); 3.31 (3H, s); 3.46 (2H, q, J=7); 3.89–3.95 (2H, m); 4.20 (2H, t, J=5); 4.75 (1H, dd, J=6.5 5.5); 6.72 (2H, d, J=8.5); 6.96 (2H, d, J=8.5); 7.01 (1H, dt, J=8.1); 7.16 (1H, dt, J=8.1); 7.26 (1H, dd, J=8.1); 7.33 (1H, dd, J=8.1); 8.00 (1H, s).

EXAMPLE 44

5-[2-[4-[2-[N-(2-Benzoxazolyl)-N-methylamino]ethoxy]phenyl]-1-ethoxy]ethyl-1,2,4-oxadiazole

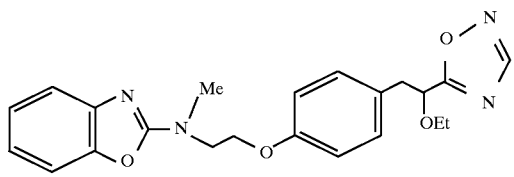

3-[4-[2-[N-(2-Benzoxazolyl)-N-methylamino]ethoxy]phenyl]-2-ethoxypropanamide (0.7 g, 1.8 mmol) in dimethylformamide dimethyl acetal (0.6 ml, 4.6 mmol) was heated to 120° C. for 1½ h. After cooling the residue was concentrated and dissolved in 70% aqueous acetic acid (2 cm$^3$). To this solution was added 5N potassium hydroxide (0.44 m) and hydroxylamine hydrochloride (152 mg) and it was then stirred for 15 minutes. After dilution with water the reaction was extracted with dichloromethane (×2) and the extracts washed with water, dried (MgSO$_4$) and concentrated. This residue was dissolved in glacial acetic acid/dioxane (2/2 ml) and heated to 90° C. for 1 hour. After dilution with water the product was extracted with chloroform (×3), the extracts washed with water (×2), dried and concentrated. Chromatography (diethyl ether/hexane) gave the product as a yellow solid m.p.=89°–90° C.

$^1$NMR δ(CDCl$_3$)

1.16 (3H, t, J=7); 3.14 (1H, g, J=14); 3.18 (1H, q, J=14); 3.34 (3H, s); 3.40–3.56 (2H, m); 3.94 (2H, t, J=5); 4.23 (2H, t, J=5); 4.75 (1H, dd, J=8.6); 6.79 (2H, d, J=9); 7.00 (1H, dt, J=7.5, 1); 7.07 (2H, d, J=9); 7.16 (1H, dt, J=7.5 1); 7.31 (1H, dd, J=7.5, 0.5); 7.35 (1H, dd, J=7.5, 0.5); 8.37 (1H, s).

EXAMPLE 45

Enantiomerically enhanced methyl 3-[4-[2-[N-(2-benzoxazolyl)-N-methylamino]ethoxy]phenyl]-2-methoxypropanoate

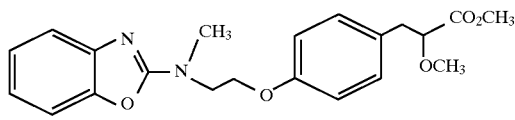

Lipase from *Rhizopus delemar* (680 mg, ex Biocatalysts Ltd.) was stirred in deionised water (380 ml) and the pH of the mixture adjusted to 7.0. To this mixture, at ambient temperature (23° C.), was added a solution of racemic methyl 3-[4-[3-[N-(2-benzoxazolyl)-N-methylamino]ethoxy]phenyl]-2-methoxypropanoate (1 g) in acetone (20 ml). The resulting reaction mixture was stirred and the pH maintained at 7.0 by autotitration with 0.1M sodium hydroxide solution. After a 66% molar equivalent of base had been added to the reaction, hydrochloric acid was added to bring the solution to pH 2.0 and the products extracted into dichloromethane. Extraction of the organic phase with 50% saturated sodium bicarbonate sodium removed the acid product and the water washed, dried (magnesium sulphate), organic phase, on evaporation, yielded 350 mg of methyl 3-[4-[2-[N-(2-benzoxazolyl)-N-methylamino]-ethoxy]phenyl]-2-methoxypropanoate as an oil with an enantiomer ratio of 5:95 as determined by chiral HPLC assay. The basic aqueous extract was acidified by the addition of hydrochloric acid and re-extracted into dichloromethane to yield, after drying and evaporation, 3-[4-[2-[N-(2-benzoxazolyl)-N-methylamino]ethoxy]phenyl]-2-methoxypropanoic acid as a white solid. This acid was stirred, at ambient temperature, for 3 hours, in methanol which had been presaturated with HCl, and the resulting methyl 3-[4-[2-[N-(2-benzoxazolyl)-N-methylamino]ethoxy]phenyl]-2-methoxypropanoate with an enantiomer ratio of 70:30, as determined by HPLC, was recovered by extraction. Enantiomer ratios of methyl 3-[4-[2-[N-(2-benzoxazolyl)-N-methylamino]ethoxy]phenyl]-2-methoxypropanoate were determined by HPLC on a chiral AGP column eluting with 12% acetonitrile in 0.01M sodium dihydrogen phosphate solution at pH 7.0 and detecting products by UV monitoring at 245 nm. Enantiomer ratios are quoted in the order of elution.

EXAMPLE 46

(+)-3-[4-[2-[N-(2-benzoxazolyl)-N-methylamino]ethoxy]phenyl]-2-methoxypropanoic acid

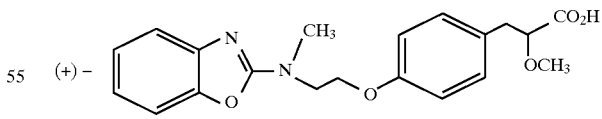

Lipase from *Rhizopus delemar* (300 mg, ex Biocatalysts Ltd.) was stirred in deionised water (125 ml) and the pH of the mixture adjusted to 7.0. To this mixture, at ambient temperature (23° C.), was added a solution of methyl 3-[4-[2-[N-(2-benzoxazolyl)-N-methylamino]ethoxy]phenyl]-2-methoxypropanoate (690 mg) (enantiomer ratio 8:92 as prepared in example 1) in acetone (5 ml). The resulting reaction mixture was stirred at ambient temperature and pH 7.0 was maintained by autotitration with 0.1M sodium hydroxide solution until hydrolysis was complete. 0.1M Sodium hydroxide solution was added to bring the reaction mixture to pH 9.5 after which it was washed with dichloromethane. The aqueous phase was acidified with hydrochloric acid to pH1 and the acid extracted into dichloromethane, washed, dried (magnesium sulphate), and evaporated. The resulting solid was triturated with hexane to yield 490 mg of (+)3-[4-[2-[N-(2-benzoxazolyl)-N-methylamino]ethoxy]phenyl]-2-methoxypropanoic acid as a white solid; m.p. 121°–123° C.; enantiomer ratio 92:8 (by HPLC assay); $[\alpha]_D^{25}$+13°, MeOH, c 0.5. Enantiomer ratios of 3-[4-[2-[N-(2-benzoxazolyl)-N-methylamino]ethoxy] phenyl]-2-methoxypropanoic acid were determined by HPLC on a chiral AGP column eluting with 4.8% acetonitrile in 0.01M sodium dihydrogen phosphate solution at pH 7.0 and detecting products by UV monitoring at 245 nm. Enantiomer ratios are quoted in the order of elution.

EXAMPLE 47

(−)-3-[4-[2-[N-(2-benzoxazolyl)-N-methylamino]ethoxy]phenyl]-2-methoxypropanoic acid

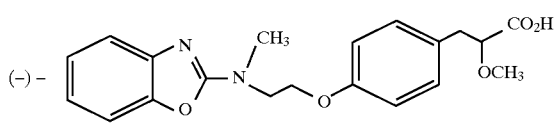

Lipase from *Rhizopus delemar* (500 mg, ex. Biocatalysts Ltd.) was stirred in deionised water (380 ml) and the pH of the mixture adjusted to 7.0. To this mixture, at ambient temperature (23° C.), was added a solution of methyl 3-[4-[2-[N-(2-benzoxazolyl)-N-methylamino]ethoxy] phenyl]-2-methoxypropanoate (950 mg) (recovered by re-esterification of acid as prepared in example 1) in acetone (20 ml). The resulting reaction mixture was stirred at ambient temperature and pH 7.0 was maintained by autotitration with 0.1M sodium hydroxide solution until a 32% molar equivalent of base had been added to the reaction then hydrochloric acid was added to bring the solution to pH 2.0 and the products extracted into dichloromethane. Extraction of the organic phase with 50% saturated sodium bicarbonate solution removed the acid product and the water washed, dried (magnesium sulphate) organic phase, on evaporation, yielded 543 mg of recovered ester. The aqueous phase was acidified with hydrochloric acid to pH1 and the acid extracted into dichloromethane, washed, dried (magnesium sulphate), and evaporated. The resulting solid was triturated with hexane to yield 256 mg of (−)-3-[4-[2-[N-(2-benzoxazolyl)-N-methylamino]ethoxy]phenyl]-2-methoxypropanoic acid as a white solid; m.p. 116°–119° C.; enantiomer ratio 7:93 (by HPLC assay); $[\alpha]_D^{25}$−10°, MeOH, c 0.55. Determination of enantiomer ratio by HPLC was as described for Example 46.

EXAMPLE 48

Ethyl (E/Z)-3-[4-[2-[N-(2-benzoxazolyl)-N-methylamino]ethoxy]-2-methoxyphenyl]-2-ethoxypropenoate

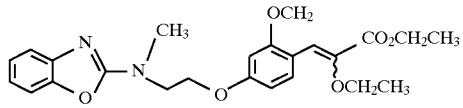

The title compound, as gum, was obtained as a 66:34 mixture of double bond isomers when triethyl 2-ethoxyphosphonoacetate was reacted with 4-[2-[N-(2-benzoxazolyl)-N-methylamino]ethoxy]-2-methoxybenzaldehyde in a manner similar to that described for Example 6.

$^1$H NMR $\delta$(CDCl$_3$)

1.09 and 1.25–1.45 (combined, 6H, OCH$_2$CH$_3$ triplets); 3.35 (3H, s); 3.75 and 3.80 (combined 3H, OMe singlets); 3.87–4.40 (8H, complex); 6.06 (0.45H, E-olefin singlet) and 6.40–8.18 (7.66H, complex, aromatic protons and Z-olefin).

EXAMPLE 49

Ethyl-3-[4-[2-[N-(2-benzoxazolyl)-N-methylamino]ethoxy]-2-methoxyphenyl]-2-ethoxypropanoate

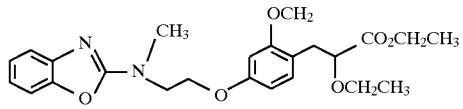

The title compound, a gum, was prepared from ethyl (E/Z)-3-[4-[2-[N-(2-benzoxazolyl)-N-methylamino]ethoxy]-2-methoxyphenyl]-2-ethoxypropenoate in a manner similar to that described for Example 8.

$^1$H NMR $\delta$(CDCl$_3$)

1.10–1.40 (6H, complex); 2.94 (2H, complex); 3.34 (3H, s); 3.35 (1H, complex); 3.55 (1H, complex); 3.76 (3H, s); 3.93 (2H, t); 4.10 (1H, dd); 4.13 (2H, q); 4.24 (2H, t); 6.39 (2H, complex) and 6.95–7.40 (5H, complex).

EXAMPLE 50

Ethyl-3-[4-[2-[N-(2-benzoxazolyl)-N-methylamino]ethoxy]-2-methoxyphenyl]-2-tert-butoxypropenoate

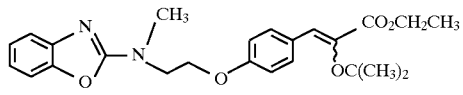

The title compound, a gum, was obtained as a 76:24 mixture of Z and E double bond isomers when triethyl 2-tert-butoxyphosphonoacetate was reacted with 4-[2-[N-(2-benzoxazolyl)-N-methylamino]ethoxy]benzaldehyde in a manner similar to that described for Example 6.

$^1$H NMR $\delta$(CDCl$_3$)

1.18 and 1.35 (combined 3H, OCH$_2$CH$_3$ triplet signals); 1.27 and 1.34 (combined 9H, OBut singlets); 3.34 and 3.35 (combined 3H, NMe singlets); 3.95 (2H, complex); 4.10–4.28 (4H, complex); 6.53 (0.24H, s, E-olefin) and 6.75–7.80 (8.76H, complex, Z-olefin and aromatic protons).

EXAMPLE 51

Ethyl 3-[4-[2-[N-(2-benzoxazolyl)-N-methylamino]ethoxy]phenyl]-2-tert-butoxypropanoate

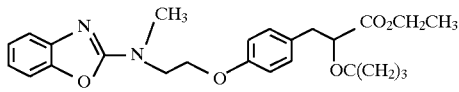

The title compound, a gum, was prepared from ethyl (E/Z)-3-[4-[2-[N-(2-benzoxazolyl)-N-methylamino]ethoxy]phenyl]-2-tert-butoxypropenoate by a method analogous to that described for Example 25. This material was contaminated with some of the corresponding methyl ester and the mixture was used directly in the next stage without further purification.

$^1$H NMR $\delta$(CDCl$_3$)

0.91 (9H, s); 1.24 (3H, t); 2.85 (2H, complex); 3.34 (3H, s); 3.93 (2H, t); 4.03 (1H, dd); 4.16 (2H, q); 4.23 (2H, t); 6.79 (2H, d) and 6.95–7.50 (6H, complex).

EXAMPLE 52

3-[4-[2-[N-(2-Benzoxazolyl)-N-methylamino]ethoxy]phenyl]-2-tert-butoxypropanoic acid

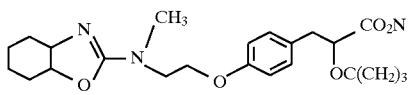

The title compound, a gum, was prepared from ethyl 3-[4-[2-[N-(2-benzoxazolyl)-N-methylamino]ethoxy]phenyl]-2-tert-butoxypropanoate by a method similar to that described in Example 2.

$^1$H NMR $\delta$(CDCl$_3$)

1.04 (9H, s); 2.84 (1H, dd); 2.98 (1H, dd); 3.34 (3H, s); 3.93 (2H, t); 4.13 (1H, dd); 4.21 (2H, t); 6.79 (2H, d); 6.95–7.40 (6H, complex) and 7.45 (1H, broad, exchanges with D$_2$O).

EXAMPLE 53

3-[4-[2-[N-(2-Benzoxazolyl)-N-methylamino]ethoxy]phenyl]-2-tert-butoxypropanoic acid, sodium salt

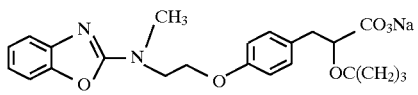

Sodium hydride (60% dispersion in mineral oil, 50 mg) was added to a stirred, ice-cooled, solution of 3-[4-[2-[N-(2-benzoxazolyl-N-methylamino]ethoxy]phenyl]-2-tert-butoxypropanoic acid (0.496 g) in methanol (10 mL). The mixture was stirred at 0° C. for 10 minutes, concentrated in vacuo and rediluted with diethyl ether (40 mL). The resulting solid was filtered and dried to afford the title compound, mp >250° C.

$^1$H NMR $\delta$(DMSO-d$_6$)

0.85 (9H, s); 2.43 (1H, dd); 2.73 (1H, dd); 3.21 (3H, s); 3.55 (1H, dd); 3.86 (2H, t); 4.19 (2H, t); 6.77 (2H, d) and 6.95–7.40 (6H, complex).

EXAMPLE 54

Ethyl (E/Z)-3-[4-[2-[N-(2-benzoxazolyl)-N-methylamino]ethoxy]phenyl]-2-(2-phenylethoxy)propenoate

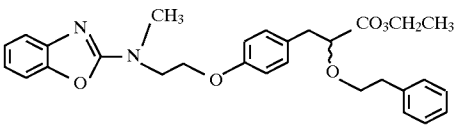

The title compound, a 71:29 Z:E mixture of double bond isomers, was obtained from triethyl 2-(2-phenylethoxy)phosphonoacetate by a method similar to that described for Example 6.

$^1$H NMR $\delta$(CDCl$_3$)

1.14 and 1.34 (combined 3H, OCH$_2$CH$_3$ triplet signals); 3.05 (2H, complex); 3.33 and 3.34 (combined 3H, NMe signals); 3.95–4.30 (8H, complex); 6.07 (0.29H, E-olefin singlet) and 6.70–7.55 (13.71H, complex, Z-olefin and aromatic protons).

EXAMPLE 55

Methyl 3-[4-[2-[N-(2-benzoxazolyl)-N-methylamino]ethoxy]phenyl]-2-(2-phenylethoxy)propanoate

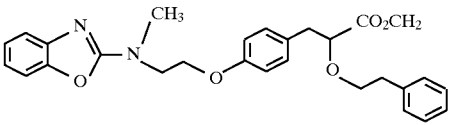

The title compound, a gum, was obtained from ethyl (E/Z)-3-[4-[2-[N-(2-benzoxazolyl)-N-methylamino]ethoxy]phenyl]-2-(2-phenylethoxy)propenoate by a method similar to that described for Example 25.

$^1$NMR $\delta$(CDCl$_3$)

2.84 (2H, t); 2.93 (2H, complex); 3.34 (3H, s); 3.43 (1H, complex); 3.68 (3H, s); 3.77 (1H, complex); 3.94 (3H, complex); 4.23 (2H, t); 6.77 (2H, d) and 6.95–7.40 (11H, complex).

EXAMPLE 56

3-[4-[2-[N-(2-Benzoxazolyl)-N-methylamino]ethoxy]phenyl]-2-(2-phenylethoxy)propanoic acid

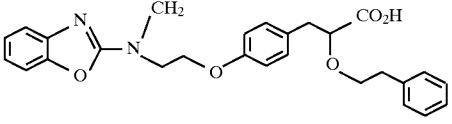

The title compound, mp 131°–3° C. (dichloromethane-hexane), was obtained from methyl 3-[4-[2-[N-(2-benzoxazolyl)-N-methylamino]ethoxy]phenyl]-2-(2-phenylethoxy)propanoic acid by a method similar to that described for Example 2.

$^1$NMR $\delta$(CDCl$_3$)

2.85 (2H, t); 2.93 (1H, dd); 3.04 (1H, dd); 3.32 (3H, s); 3.57 (1H, complex); 3.77 (1H, complex); 3.91 (2H, t); 4.02 (1H, dd); 4.17 (2H, t); 6.10 (1H, broad, exchanges with D$_2$O); 6.77 (2H, d) and 6.95–7.40 (11H, complex).

EXAMPLE 57

Ethyl (E/Z)-3-[4-[2-[N-(2-benzoxazolyl)-N-methylamino]ethoxy]phenyl]-2-(2-methoxyethoxy)propenoate

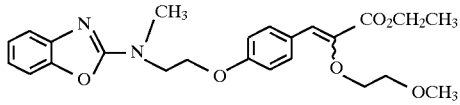

The title compound, a gum, was obtained as a 76:24 Z-E mixture of double bond isomers from triethyl 2-(2-methoxyethoxy)phosphonoacetate by a method similar to that described for Example 6.

$^1$H NMR δ(CDCl$_3$)

1.12 and 1.35 (combined 3H, OCH$_2$CH$_3$ triplets); 3.35–3.45 (combined, 6H, complex NME and OMe singlets); 3.67 and 3.72 (combined 2H, complex, OCH$_2$CH$_2$OMe signals); 3.90–4.35 (8H, complex); 6.15 (0.24HE-olefin singlet) and 6.80–7.80 (8.76H, complex).

EXAMPLE 58

Methyl 3-[4-[2[N-(2-benzoxazolyl)-N-methylamino]ethoxy]phenyl]-2-(2-methoxyethoxy)propanoate

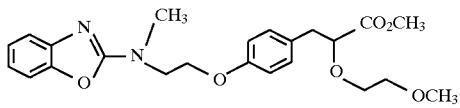

The title compound, a gum, was prepared from ethyl (E/Z)-3-[4-[2-[N-(2-benzoxazolyl)-N-methylamino]ethoxy]phenyl]-2-(2-methoxyethoxy)propanoate by a method similar to that described for Example 25.

$^1$H NMR δ(CDCl$_3$)

2.95 (2H, complex); 3.29 (3H, s); 3.34 (3H, s); 3.47 (3H, complex); 3.68 (1H, complex); 3.69 (3H, s); 3.93 (2H, t); 4.06 (1H, dd); 4.23 (2H, t); 6.79 (2H, d); and 6.95–7.40 (6H, complex).

EXAMPLE 59

Methyl (Z)-3-[4-[2-[N-(2-benzoxazolyl)-N-methylamino]ethoxy]phenyl]-2-(carboxymethoxy)propenoate

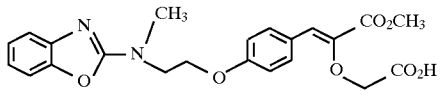

A mixture of sodium hydride (60% dispersion in mineral oil. 0.30 g), dimethyl diglycolate (0.81 g) and 4-[2-[N-(2-benzoxazolyl)-N-methylamino]ethoxy]benzaldehyde (2.22 g) in dry benzene (50 mL) was stirred at room temperature overnight. Acetic acid (1 mL) was added, the mixture was poured onto iced water and extracted with ethyl acetate. The combined ethyl acetate layers were washed with water, dried (MgSO$_4$) and evaporated. The resulting oil was chromatographed on silica gel using 2% methanol in dichloromethane, and the product crystallised from ethyl acetate, mp 111°–112° C.

$^1$H NMR δ(CDCl$_3$) 3.34 (3H,s); 3.83 (3H,s); 3.95 (2H,t); 4.25 (2H,t); 4.51 (2H,s); 6.85–7.50 (9H, complex) and 9.40 (1H, broad, exchanges with D$_2$O).

EXAMPLE 60

Methyl 3-[4-[2-[N-(2-benzoxazolyl)-N-methylamino]ethoxy]phenyl]-2-(carboxymethoxy)propanoate

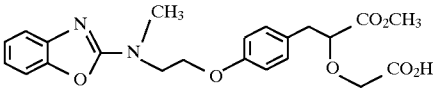

The title compound, mp 154°–155° C., was prepared from methyl (Z)-3-[4-[2-[N-(2-benzoxazolyl)-N-methylamino]ethoxy]phenyl]-2-(carboxymethoxy)propenoate by a method similar to that described for Example 8.

$^1$H NMR δ (CDCl$_3$) 2.95 (1H,dd); 3.09 (1H,dd); 3.31 (3H,s); 3.75 (3H,s); 3.93 (2H,complex); 4.07 (2H,s); 4.20 (3H, complex); 6.79 (2H,d) and 6.95–7.40 (7H, complex, reduces to 6H on shaking with D$_2$O).

EXAMPLE 61

5-[2-[4-[2-[N-(2-Benzoxazolyl)-N-methylamino]ethoxy]phenyl]-1-ethoxyethyl]-3methyl-1,2,4-oxadiazole

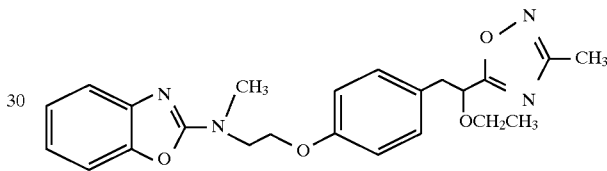

The title compound, mp 61°–62° C., was prepared in a manner analogous to that described for Example 44 using N,N-dimethylacetamide dimethyl acetal in place of N,N-dimethylformamide dimethyl acetal.

$^1$H NMR δ (CDCl$_3$) 1.15 (3H,t); 2.39 (3H,s); 3.12 (1H,q); 3.14 (1H,q); 3.35 (3H,s); 3.35–3.60 (2H,m); 3.94 (2H,t); 4.23 (2H,t); 4.65 (1H,dd); 6.79 (2H,d) and 7.00–7.36 (6H, complex).

EXAMPLE 62

5-[2-[4-[N-(2-Benzoxazolyl)-N-methylamino]ethoxy]phenyl]-1-ethoxyethyl]-1,2,3,4-(1H)-tetrazole

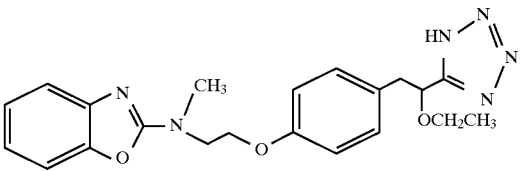

Sodium azide (0.76 g) and trimethylsilyl chloride (1 mL) were added to a solution of 3-[4-[2-[N-(2-benzoxazolyl)-N-methylamino]ethoxy]phenyl]-2-ethoxypropanonitrile (0.85 g) in N,N-dimethyl formamide (30 mL). The mixture was refluxed for 4 days, cooled, poured into water and extracted with ethyl acetate. The combined ethyl acetate layers were washed with water, dried and evaporated. The residue was purified by chromatograhy on silica gel using 1% methanol in ether as solvent to afford the title compound, a white foam.

$^1$H NMR δ (CDCl$_3$) 1.13 (3H,t); 3.13 (2H,dd); 3.22 (3H,s); 3.51 (2H,dq); 3.88 (2H,t); 4.15–4.20 (2H,m); 4.99 (1H,t); 6.22 (2H,d); 6.80 (2H,d); 7.04 (1H,dt); 7.16 (1H,dt) and 7.25–7.31 (2H,m).

PROCEDURE 1

Ethyl 3-(4-hydroxyphenyl)-2-methoxypropanoate

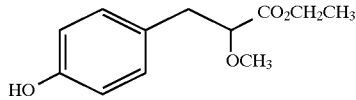

A solution of ethyl 2-diazo-3-(4-hydroxyphenyl) propanoate (c.f. N. Takamura and T. Mizoguchi, *Tetrahedron Lett.* 1971, 4495) (8.8 g) in benzene (40 mL) was added over 30 minutes to a stirred, refluxing mixture of rhodium (II) acetate dimer (10 mg), methanol 7.9 mL) and benzene (50 mL). The mixture was heated at reflux for a further 30 minutes, then allowed to cool to room temperature overnight and washed with water (2×200 mL). The benzene solution was dried (MgSO$_4$) and evaporated and the residual oil chromatographed twice on silica gel, firstly with 20% ethyl acetate in hexane as eluent and subsequently with 4% ethyl acetate in dichloromethane as eluent to afford the title compound as an oil.

$^1$H NMR δ (CDCl$_3$) 1.22 (3H,t); 2.94 (2H, d); 3.35 (3H,s); 3.94 (1H, t); 4.20 (2H, q); 5.73 (1H, exchanges with D$_2$O); 6.75 (2H, d); and 7.15 (2H, d).

PROCEDURE 2

Methyl 3-(4hydroxyphenyl)-2-methoxypropanoate

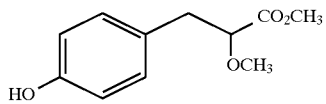

A solution of methyl 2-diazo-3-(4-hydroxyphenyl) propanoate (cf *Tetrahedron Lett.*, 1971, 4495) (8.58 g) in methanol (120 mL) was added over 10 minutes to a mixture of rhodium (II) acetate dimer (0.18 g) in methanol (50 mL) at room temperature under a nitrogen atmosphere. The resulting mixture was heated at reflux for 5 hrs, allowed to stand at room temperature for 15 hrs, then concentrated in vacuo. The residue was dissolved in ethyl acetate (500 mL), washed with water (3×300 mL) and brine (500 mL), dried (MgSO$_4$) and evaporated. The resulting gum was chromatographed on silica gel with a gradient of 4% ethyl acetate to 6% ethyl acetate in dichloromethane as eluent to afford the title compound. mp 61°–3° C.

$^1$H NMR δ (CDCl$_3$) 2.95 (2H,d); 3.40 (3H,s); 3.75 (3H,s); 4.00 (1H,t); 6.30 (1H,broad, exchanges with D$_2$O); 6.80 (2H,d); and 7.15 (2H,d).

PROCEDURE 3

(E/Z)-1-Methoxy-2-[4-[2-[N-methyl-N-(2-pyridyl) amino]ethoxy]-phenyl]ethane

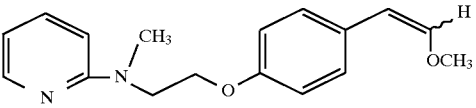

Methoxymethyltriphenylphosphonium chloride (12.34 g) was suspended in dry terahydrofuran (200 mL), cooled to −10° C. and stirred under a nitrogen atmosphere during the addition of a solution of lithium diisopropylamide (2.0M in heptane/tetrahydrofuran/ethyl benzene; 13.5 mL) over ca 5 minutes. The resulting mixture was allowed to warm to 10° C., and stirred at this temperature for 1 hr. A solution of 4-[2-[N-methyl-N-(2-pyridyl)amino]ethoxy]benzaldehyde (Eur. Patent Appl. Publication No. 0306228) (4.60 g) in dry temperature (75 mL) was added at 10° C. and the mixture then stirred at room temperature for 4.5 hrs. The solvent was evaporated, the residue suspended in water (600 mL) and extracted with dichloromethane (3×250 mL). The combined dichloromethane solutions were washed with water (3×1 L) and brine (1 L), dried (MgSO$_4$) and evaporated. The residue was chromatographed on silica gel with 1.5% gel methanol in dichloromethane as eluent to afford the title compound, a gum, as a 1:1 mixture of double bond isomers.

$^1$H NMR δ (CDCl$_3$) (Z)-alkene: 3.12 (3H,s); 3.72 (3H,s); 3.94 (2H,t); 4.14 (2H,t); 5.14 (1H,d,J=7.0 Hz); 6.01 (1H,d, J=7.0 Hz); 6.48 (2H, complex); 6.80 (2H,d); 7.11 (2H,d); 7.45 (1H,complex); and 8.15 (1H,dd).

(E)-alkene: 3.12 (3H,s); 3.63 (3H,s); 3.94 (2H,t); 4.15 (2H,t); 5.74 (1H,d,J=12.9 Hz); 6.49 (2H,complex); 6.80 (2H,d); 6.88 (1H,d,J=12.9 Hz); 7.45 (3H,complex); and 8.15 (1H,dd).

PROCEDURE 4

1,1-Dimethoxy-2-[4-[2-[N-methyl-N-(2-pyridyl) amino]ethoxy]-phenyl]ethane

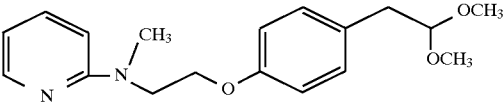

A mixture of (E/Z)-1-methoxy-2-[4-[2-[N-methyl-N-(2-pyridyl)amino]ethoxy]phenyl]ethene (2.80 g), p-toluenesulphonic acid monohydrate (1.90 g) and methanol (150 mL) was heated at reflux for 20.75 hrs, cooled and evaporated. The residue was dissolved in ethyl acetate (200 mL), washed with saturated sodium bicarbonate solution (200 mL) and brine (200 mL), dried (MgSO$_4$) and evaporated. The title compound, a gum, was used in the next stage without purification.

$^1$H NMR δ (CDCl$_3$) 2.85 (2H,d); 3.15 (3H,s); 3.33 (6H,s); 3.98 (2H,t); 4.20 (2H,t); 4.49 (1H,t); 6.50–7.50 (7H, complex); and 8.20 (1H,dd).

PROCEDURE 5

2-Methoxy-3-[4-[2-[N-methyl-N-(2-pyridyl)amino] ethoxy]-phenyl]propanonitrile

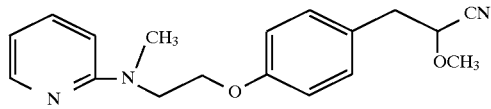

Trimethylsilyl cyanide (3.4 mL) was added dropwise to a solution of 1,1-dimethoxy-2-[4-[2-[N-methyl-N-(2-pyridyl) amino]ethoxy]phenyl]ethane (2.64 g) in dichloromethane (70 mL) at room temperature. The mixture was stirred during the addition of boron trifluoride etherate (0.3 mL), and stirring continued at room temperature for 1.5 hrs. prior to the addition of a further portion of boron trifluoride etherate (1 mL). After a further 2 hours the mixture was diluted with dichloromethane (100 mL) and washed with saturated sodium bicarbonate solution (2×300 mL), water (2×300 mL) and brine (300 mL), dried (MgSO$_4$) and evaporated. The residue was chromatographed on silica gel with 1% methanol in dichloromethane as eluent to afford the title compound, a gum, which was used without further purification.

$^1$H NMR δ (CDCl$_3$) 3.04 (2H,d); 3.14 (3H,s); 3.46 (3H,s); 3.96 (2H,s); 4.16 (3H,complex); 6.55 (2H,complex); 6.84 (2H,d); 7.15 (2H,d); 7.45 (1H,td); and 8.15 (1H,dd).

PROCEDURE 6

Methyl 2-amino-3-[4-[2-[N-(2-benzoxazolyl)-N-methylamino]ethoxy]phenyl]propanoate

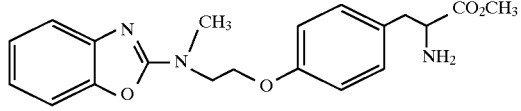

Sodium hydride (60% dispersion in oil; 1.00 g) was added portionwise to stirred solution of tyrosine methyl ester (3.90 g) in dry N,N-dimethylformamide (70 mL) under a nitrogen atmosphere. The mixture was stirred at room temperature for 30 minutes prior to the addition of a solution of 2-[N-(2-benzoxazolyl)-N-methylamino]ethanol methanesulphonyl ester (Eur. Patent Appl. Publication No. 0306228) (5.90 g) in dry N,N-dimethylformamide (30 mL). The mixture was heated at 100° C. for 6 hrs, cooled, diluted with iced water (500 mL) and extracted with ethyl acetate (3×250 mL). The combined ethyl acetate layers were washed with brine (2×1 L), dried (MgSO$_4$) and evaporated. The residue was chromatographed on silica gel with 5% methanol in dichloromethane as eluent to afford an oil. This was crystallised from ethyl acetate to afford the title compound, mp 95°–6° C.

PROCEDURE 7

Methyl 3-[4-[2-[N-(2-benzoxazolyl)-N-methylamino]ethoxy]phenyl]-2-diazopropanoate

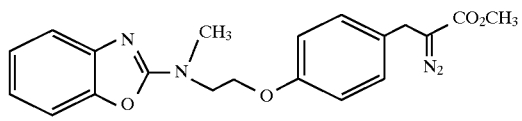

A mixture of methyl 2-amino-3-[4-[2-[N-(2-benzoxazolyl)-N-methylamino]ethoxy]phenyl]propanoate (5.00 g), acetic acid (4.4 mL) and chloroform (160 mL) was treated dropwise with isoamyl nitrite (3.2 mL). The mixture was heated at reflux for 1.5 hrs, cooled, diluted with chloroform (200 mL) and washed successively with dilute hydrochloric acid (200 mL), water (2×200 mL) and brine (200 mL). The chloroform solution was dried over MgSO$_4$, evaporated and the residue chromatographed on silica gel using 3% ethyl acetate in dichloromethane as eluent to afford the title compound, a gum.

$^1$H NMR δ (CDCl$_3$) 3.34 (3H,s); 3.56 (2H,s); 3.77 (3H,s); 3.94 (2H,t); 4.25 (2H,t); and 6.80–7.40 (8H,complex).

PROCEDURE 8

Methyl 3-(4-hydroxyphenyl)-2-isopropoxypropanoate

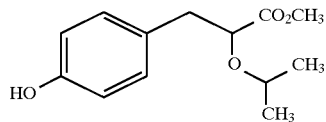

The title compound, a gum, was prepared from methyl 2-diazo-3-(4-hydroxyphenyl)propanoate (3.00 g) by a method similar to that described in Procedure 2.

$^1$H NMR δ (CDCl$_3$) 0.97 (3H,d); 1.14 (3H,d); 2.91 (2H,complex); 3.51 (1H,complex), 3.71 (3H,s); 4.05 (1H, dd); 6.02 (1H,br,exchanges with D$_2$O); 6.75 (2H,d); and 7.08 (2H,d).

PROCEDURE 9

Methyl 3-(4-hydroxyphenyl)-2-propoxypropanoate

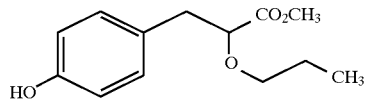

The title compound, an oil, was prepared from methyl 2-diazo-3-(4-hydroxyphenyl)propanoate (2.56 g) by a method similar to that described in Procedure 2.

$^1$H NMR δ (CDCl$_3$) 0.83 (3H,t); 1.54 (2H,complex); 2.93 (2H,app.d); 3.22 (1H,complex); 3.51 (1H,complex); 3.71 (3H,s); 3.99 (1H,t); 5.54 (1H,br,exchanges with D$_2$O): 6.74 (2H,d); and 7.08 (2H,d).

PROCEDURE 10

Methyl 2-hydroxy-3-(4-hydroxyphenyl)propanoate

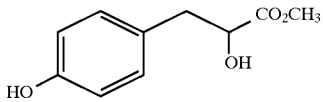

A solution of methyl 3-(4-benzyloxyphenyl)-2-hydroxypropanoate (c.f. International Patent Appl., Publication No. WO 9101337) (5.72 g) in methanol (120 mL was added to an ice cooled suspension of 10% Palladium charcoal (1.90 g) in methanol (30 mL) under a nitrogen atmosphere. Solid ammonium formate (6.4 g) was added and the mixture heated at reflux for 15 minutes, then allowed to cool to room temperature. The catalyst was removed by filtering the reaction mixture through diatomaceous earth and the solvent evaporated. The residue was suspended in dilute hydrochloric acid (2M, 100 mL) and extracted with ethyl acetate (2×400 mL). The combined ethyl acetate solutions were washed with water (400 mL), brine (400 mL), dried (MgSO$_4$) and evaporated. The resulting gum was chromatographed on silica gel with 1.5% methanol in dichloromethane as eluent to afford the title compound, mp 42°–43° C.

$^1$H NMR d(CDCl$_3$) 2.85 (1H, broad, exchanges with D$_2$O); 2.90 (1H,dd); 3.05 (1H, dd); 3.77 (3H, s); 4.42 (1H, m, collapses to dd on washing with D$_2$O); 5.36 (1H, broad, exchanges with D$_2$O); 6.70 (2H, d); and 7.05 (2H, d).

PROCEDURE 11

Methyl 3-[4-[2-[N-(2-benzoxazolyl)-N-methylamino]ethoxy]phenyl]-2-hydroxypropanoate

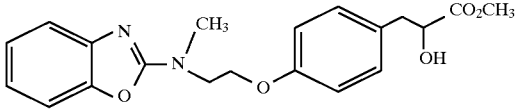

The title compound, mp 10°–112° C., was prepared from methyl 2-hydroxy-3-(4-hydroxyphenyl)propanoate by a procedure similar to that described in Example 1.

$^1$H NMR d (CDCl$_3$) 2.68 (1H, d, exchanges with D$_2$O); 2.90 (1H, dd); 3.05 (1H, dd); 3.35 (3H, s); 3.76 (3H, s); 3.95 (2H, t); 4.25 (2H, t); 4.41 (1H, m, collapses to dd on washing with D$_2$O); 6.81 (2H, d); and 6.96–7.40 (6H, complex).

PROCEDURE 12

Methyl 2-[4-[2-[N-(2-benzoxaxolyl)-N-methylamino]ethoxy]phenyl]ethanoate

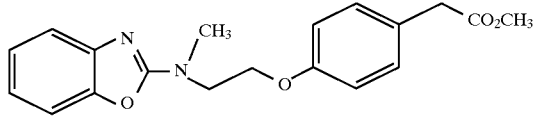

Sodium hydride (60% dispersion in mineral oil, 2.20 g) was added portionwise to a stirred solution of methyl 4-hydroxyphenylethanoate (8.30 g) in dry N,N-dimethyl formamide (100 mL) at room temperature under a nitrogen atmosphere. The mixture was stirred at this temperature for 30 minutes prior to the addition of a solution of 2-[N-(2-benzoxazolyl)-N-methylamino]ethanol methanesulphonyl ester (13.50 g) in N,N-dimethyl formamide (150 mL). The mixture was heated at 80° C. for 18 hours, cooled and concentrated in vacuo. The residue was diluted with water (1 L), extracted with ethyl acetate (3×400 mL) and the combined ethyl acetate solutions washed with water (4×1 L), brine (1 L), dried (MgSO$_4$) and evaporated. The residue was chromatographed on silica gel using 1.5% methanol in dichloromethane as solvent to afford the title compound as a gum which was used without further purification.

$^1$H NMR δ(CDCl$_3$) 3.35 (3H,s); 3.57 (2H,s); 3.70 (3H,s); 3.93 (2H,t); 4.28 (2H,t); and 6.85–7.45 (8H, complex).

PROCEDURE 13

2-[4-[2-[N-(2-Benzoxazolyl)-N-methylamino]ethoxy]phenyl]ethanol

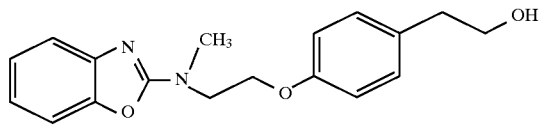

A solution of methyl 2-[4-[2-[N-(2-benzoxazolyl)-N-methylamino]ethoxy]phenyl]ethanoate (11.60 g) in dry diethyl ether (200 mL) was added slowly to an ice-cooled, stirred suspension of lithium aluminium hydride (1.36 g) in ether (50 mL) under a nitrogen atmosphere. The mixture was stirred at 0° C. for 20 minutes, then water (10 mL) and hydrochloric acid (2M; 10 mL) were added dropwise with caution. The mixture was diluted with water (200 mL) was the solution adjusted to pH 4 prior to extraction with ethyl acetate (3×200 mL). The combined ethyl acetate solutions were washed with water (2×500 mL), brine (500 mL), dried (MgSO$_4$) and evaporated to afford the title compound, mp 95°–97° C.

$^1$H NMR δ(CDCl$_3$) 2.15 (1H,broad,exchanges with D$_2$O); 2.75 (2H,t); 3.30 (3H,s); 3.80 (2H,t); 3.97 (2H,t); 4.22 (2H,t); and 6.80–7.45 (8H,complex).

PROCEDURE 14

4-[2-[N-(2-Benzoxazolyl)-N-methylamino]ethoxy]phenylethanal

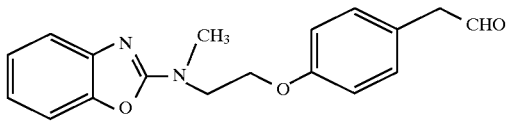

A solution of pyridine-sulphur trioxide complex (1.53 g) in dimethylsulphoxide (5 mL) was added to a stirred, ice cooled mixture of 2-[4-[2-[N-(2-benzoxazolyl)-N-methylamino]ethoxy]phenyl]ethanol (1.00 g), triethylamine (2.25 mL) and dichloromethane (30 mL) under a nitrogen atmosphere. The mixture was stirred at 0° C. for 10 minutes, then at room temperature for 5 hours before being diluted with dichloromethane (100 mL) and washed with water (2×100 mL), hydrochloric acid (0.5M; 100 mL), water (2×100 mL) and brine (100 mL), dried (MgSO$_4$) and evaporated. The residue was chromatographed on silica gel with 5% ethyl acetate in dichloromethane as solvent to afford the title compound, a gum.

¹H NMR δ(CDCl₃) 3.29 (3H,s); 3.53 (2H,d); 3.86 (2H,t); 4.19 (2H,t); 6.80–7.50 (8H, complex); and 9.68 (1H,t).

PROCEDURE 15

Methyl 3-(4-hydroxyphenyl)-2-(2,2,2-trifluoroethoxy)propanoate

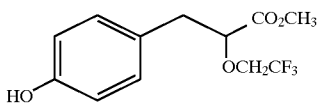

A solution of methyl 2-diazo-3-(4-hydroxyphenyl) propanoate (3.00 g) in 2,2,2-trifluoroethanol (10 mL) was slowly added, over 15 minutes, to a stirred mixture of rhodium (II) acetate dinner (0.064 g) and 2,2,2-trifluoroethanol (5 mL) at room temperature under a nitrogen atmosphere. The mixture was stirred at temperature for 15 minutes, then heated at reflux for 4 hours, cooled and evaporated. The residue was chromatographed on silica gel with 4% ethyl acetate in dichloromethane to afford the title compound, a gum, which was used without further purification.

¹H NMR δ(CDCl₃) 3.00 (2H,complex); 3.65 (1H, complex); 3.74 (3H,s); 4.00 (1H,complex); 4.17 (1H,dd); 5.20 (1H,broad,exchanges with D₂O); 6.75 (2H,d); and 7.08 (2H,d).

Mass spectrum (EI) shows M⁺ at 2.78.0763 amu; $C_{12}H_{13}F_3O_4$ requires 278.0766.

PROCEDURE 16

3-[4-[2-[N-(2-Benzoxazolyl)-N-methylamino]ethoxy]phenyl]-2-ethoxypropanotrile

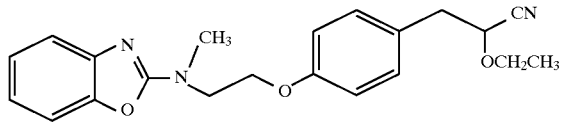

A mixture of 4-[2-[N-(2-benzoxazolyl)-N-methylamino]ethoxy]phenylethanal (1.5 g), p-toluenesulphonic acid monohydrate (100 mg), 3A molecular sieves (2 g) and ethanol (30 ml) was heated at reflux for 18 hours, cooled and stirred with potassium carbonate (5 g) for 30 minutes. The mixture was filtered through celite and evaporated to afford (3-[4-[2-[N-(2-benzoxazolyl)-N-methylamino]ethoxy]phenyl]ethanal diethyl acetal, which was used without further purification (below).

Boron trifluoride etherate (0.05 ml) was added to a cold (4° C.) solution of the above acetal (1.5 g) and trimethylsilyl cyanide (0.5 mL) in dichloromethane (20 mL). The mixture was warmed to room temperature and stirred for 24 hrs before being poured into aqueous sodium bicarbonate solution. The organic phase was separated, dried (MgSO₄) and evaporated. The residual oil was chromatographed on silica gel using 20% ether in dichloromethane as eluent to afford the title compound as an oil.

¹H NMR δ(CDCl₃) 1.20 (3H,t); 3.05 (2H,d); 3.30 (3H,s); 3.3–4.8 (2H,complex); 3.87 (2H,t); 4.10–4.30 (3H, complex); 6.82 (2H,d) and 6.90–7.40 (6H,complex).

Demonstration of Efficacy of Compounds
Obese Mice, Oral Glucose Tolerance Test

C57bl1/6 obese (ob/ob) mice were fed on powdered oxoid diet. After at least one week, the mice continued on a powdered oxoid diet or were fed powered oxoid diet containing the test compound. After 8 days on the supplemented diet all of the mice were fasted for 5 hours prior to receiving an oral load of glucose (3 g/kg). Blood samples for glucose analysis were taken 0,45,90 and 135 minutes after glucose administration and the results appear below as the percentage reduction in area under the blood glucose curve were test compound groups are compared with the control group. 8 mice were tested for each treatment.

TABLE

| Example | Level in diet ($\mu$mol. kg⁻¹ of diet) | % Reduction in area under blood glucose curve |
|---|---|---|
| 1 | 3000 | 54 |
|   | 30 | 49 |
| 2 | 3000 | 51 |
|   | 30 | 58 |
| 3 | 100 | 53 |
| 4 | 300 | 55 |
|   | 30 | 49 |
| 5 | 100 | 51 |
| 6 | 1000 | 50 |
|   | 30 | 26 |
| 9 | 100 | 49 |
| 10 | 100 | 53 |
|   | 10 | 56 |
| 11 | 100 | 51 |
|   | 30 | 49 |
| 14 | 30 | 54 |
| 17 | 100 | 52 |
| 20 | 100 | 58 |
| 23 | 100 | 58 |
| 26 | 100 | 51 |
| 29 | 100 | 60 |
|   | 30 | 55 |
| 31 | 30 | 41 |
| 34 | 100 | 36 |
| 35 | 1000 | 59 |
| 37 | 30 | 61 |
| 38 | 10 | 56 |
| 40 | 10 | 62 |
| 41 | 30 | 61 |
| 42 | 30 | 69 |
| 43 | 100 | 56 |
| 44 | 300 | 37 |
| 46 | 30 | 57 |
| 47 | 30 | 61 |
| 49 | 30 | 53 |
| 61 | 10 | 37 |

We claim:
1. A compound of formula (I):

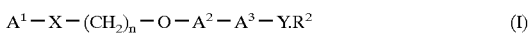

or a tautomeric form thereof a pharmaceutically salt thereof, a pharmaceutically acceptable solvate thereof, wherein:
A¹ represents a moiety of formula (b)

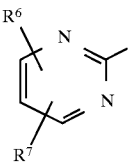

wherein:
R⁶ and R⁷ each independently represents a hydrogen or halogen atom, an alkyl or alkoxy group or a substituted or unsubstituted aryl group or when R⁶ and R⁷ are each attached to adjacent carbon atoms, then $R^6$ and $R^7$ together with the carbon atoms to which they are attached form a benzene ring wherein each carbon atom represents by $R^6$ and $R^7$ together is substituted or unsubstituted;

$A^2$ represents a benzene ring having three optional substituents;

$A^3$ represents a moiety of formula $-(CH_2)_m-CH(OR^1)-$ wherein $R^1$ represents substituted or unsubstituted alkyl, aryl, aralkyl or alkylcarbonyl and m represents an integer in the range of from 1 to 5, or $A^3$ represents a moiety of formula $-(CH_2)_{m-1}-CH=C(OR^1)-$ wherein $R^1$ and m are as defined above;

$R^2$ represents $OR^3$ wherein $R^3$ represents hydrogen, alkyl, aryl or aralkyl or $R^2$ represents an aromatic heterocyclyl group or $-NR^4R^5$ wherein $R^4$ and $R^5$ each independently represent hydrogen, alkyl or alkylcarbonyl or $R^4$ and $R^5$ together with the nitrogen atom to which they are attached form a heterocyclic ring;

X represents NR wherein R represents a hydrogen atom, an alkyl group, an acyl group, an aralkyl group wherein the aryl moiety may be substituted or unsubstituted, or a substituted or unsubstituted aryl group;

Y represents CO or CS or a bond providing that Y represents a bond only when $R^2$ represents the above mentioned aromatic heterocyclyl group; and n represents an integer in the range of from 2 to 6.

2. A compound according to claim 1, wherein A3 represents a moiety of formula $-(CH_2)_m-CH(OR^1)-$.

3. A compound according to claim 1, wherein $A^3$ represents a moiety of formula $-CH=C(OR^1)-$.

4. A compound according to claim 1, wherein $R^1$ represents substituted or unsubstituted alkyl or substituted or unsubstituted aralkyl.

5. A compound according to claim 1, wherein $R^1$ is unsubstituted alkyl or unsubstituted aralkyl.

6. A compound according to claim 1, wherein $R^1$ is ethyl or benzyl.

7. A compound according to claim 1, wherein $R^2$ represents $OR^3$.

8. A compound according to claim 7, wherein $R^3$ represents hydrogen or alkyl.

9. A compound according to claim 1, wherein m is 1 and n is 2.

10. An enantiomerically enriched compound according to claim 1 wherein $A^3$ represents $(CH_2)_m-CH(OR^1)-$, Y represents CO, $R^2$ is $OR^3$ and $A^1$, $A^2$, $R^1$, $R^3$, X, m and n are as defined in relation to formula (I) as defined in claim 1, or a tautomeric form thereof and/or a pharmaceutically acceptable salt thereof and/or a pharmaceutically acceptable solvate thereof.

11. A compound of formula (IA) according to claim 10, or a tautomeric form thereof and/or a pharmaceutically acceptable salt thereof and/or a pharmaceutically acceptable solvate thereof, in optically pure form.

12. A pharmaceutical composition comprising a compound according to claim 1, or a tautomeric form thereof, or a pharmaceutically acceptable salt thereof, or a pharmaceutically acceptable solvate thereof, and a pharmaceutically acceptable carrier therefor.

13. A method for the treatment and/or prophylaxis of hyperglycaemia in a human or non-human mammal which comprises administering an effective, non-toxic, amount of a compound according to claim 1, or a tautomeric form thereof and/or a pharmaceutically acceptable salt thereof and/or a pharmaceutically acceptable solvate thereof to a hyperglycaemic human or non-human mammal in need thereof.

* * * * *